US010052489B2

United States Patent
Katra et al.

(10) Patent No.: US 10,052,489 B2
(45) Date of Patent: Aug. 21, 2018

(54) APPARATUS AND METHOD FOR IMPLANTING AN IMPLANTABLE DEVICE

(71) Applicant: Greatbatch Ltd., Clarence, NY (US)

(72) Inventors: Rodolphe Katra, Blaine, MN (US);
Scott Kimmel, Roseville, MN (US);
Lawrence Kane, St. Paul, MN (US);
Daniel Chase, Minneapolis, MN (US)

(73) Assignee: Greatbatch Ltd., Clarence, NY (US)

( * ) Notice: Subject to any disclaimer, the term of this patent is extended or adjusted under 35 U.S.C. 154(b) by 425 days.

(21) Appl. No.: 14/665,309

(22) Filed: Mar. 23, 2015

(65) Prior Publication Data
US 2016/0279397 A1    Sep. 29, 2016

(51) Int. Cl.
| A61B 17/34 | (2006.01) |
| A61M 25/06 | (2006.01) |
| A61N 1/372 | (2006.01) |
| A61B 17/32 | (2006.01) |
| A61N 1/05 | (2006.01) |

(52) U.S. Cl.
CPC ..... *A61N 1/37229* (2013.01); *A61M 25/0668* (2013.01); *A61B 17/3468* (2013.01); *A61B 2017/320044* (2013.01); *A61B 2017/320056* (2013.01); *A61N 1/0504* (2013.01)

(58) Field of Classification Search
CPC ...... A61M 25/0194; A61M 2025/0197; A61M 25/0668; A61M 2025/0034; A61N 1/0504; A61B 5/042; A61B 5/0452–5/0492; A61B 5/1459; A61B 5/1473; A61B 5/14865
See application file for complete search history.

(56) References Cited

U.S. PATENT DOCUMENTS

| 3,943,936 A | 3/1976 | Rasor et al. |
| 4,453,537 A | 6/1984 | Spitzer |
| 4,687,469 A | 8/1987 | Osypka |
| 4,716,903 A | 1/1988 | Hansen et al. |

(Continued)

FOREIGN PATENT DOCUMENTS

| WO | 8002231 | 10/1980 |
| WO | 2004041124 | 5/2004 |

OTHER PUBLICATIONS

Intsearch, "PCT2009032640", Apr. 15, 2009, Dated Apr. 15, 2009.

*Primary Examiner* — Darwin Erezo
*Assistant Examiner* — Jonathan Hollm
(74) *Attorney, Agent, or Firm* — Michael P. Horvath

(57) ABSTRACT

In various examples, an apparatus is configured for subcutaneously inserting an implantable device within a patient. The apparatus includes a dilator portion including a dilator including a dilator length. The dilator portion is configured to separate tissue to create a subcutaneous pocket within the patient sized and shaped to accommodate an implantable device within the subcutaneous pocket. A sheath portion includes a sheath sized and shaped to accommodate the dilator within a sheath lumen. The sheath is configured to accommodate an antenna of the implantable device with the dilator removed from within the sheath. The sheath includes a sheath length that is at least substantially as long as an antenna length. The sheath is configured to separate to allow removal of the sheath around the implantable device to remove the sheath from and leave the implantable device within the subcutaneous pocket within the patient.

18 Claims, 11 Drawing Sheets

(56) References Cited

U.S. PATENT DOCUMENTS

| | | | |
|---|---|---|---|
| 4,921,479 A * | 5/1990 | Grayzel | A61M 25/0668 604/160 |
| 4,974,600 A | 12/1990 | Reyes | |
| 5,113,869 A | 5/1992 | Nappholz et al. | |
| 5,269,326 A | 12/1993 | Verrier | |
| 5,313,953 A | 5/1994 | Yomtov et al. | |
| 5,324,312 A | 6/1994 | Stokes et al. | |
| 5,645,586 A | 7/1997 | Meltzer | |
| 5,741,211 A | 4/1998 | Renirie et al. | |
| 5,833,603 A | 11/1998 | Kovacs et al. | |
| 5,987,352 A | 11/1999 | Klein et al. | |
| 6,027,480 A * | 2/2000 | Davis | A61M 25/0606 604/164.05 |
| 6,285,897 B1 | 9/2001 | Kilcoyne et al. | |
| 6,347,245 B1 | 2/2002 | Lee et al. | |
| 6,379,346 B1 * | 4/2002 | McIvor | A61M 25/0668 604/524 |
| 6,436,068 B1 | 8/2002 | Bardy | |
| 6,445,952 B1 | 9/2002 | Manrodt et al. | |
| 6,480,733 B1 | 11/2002 | Turcott | |
| 6,496,715 B1 | 12/2002 | Lee et al. | |
| 6,699,200 B2 | 3/2004 | Cao et al. | |
| 6,950,705 B2 | 9/2005 | Bardy et al. | |
| 7,107,093 B2 | 9/2006 | Burnes | |
| 7,107,103 B2 | 9/2006 | Schulman et al. | |
| 7,212,849 B2 | 5/2007 | Zhang et al. | |
| 7,299,086 B2 | 11/2007 | McCabe et al. | |
| 8,180,438 B2 | 5/2012 | Brockway et al. | |
| 8,280,499 B2 | 10/2012 | Brockway et al. | |
| 9,161,775 B1 * | 10/2015 | Katra | A61B 17/3209 |
| 2001/0047314 A1 | 11/2001 | Linberg | |
| 2002/0035381 A1 | 3/2002 | Bardy et al. | |
| 2002/0040231 A1 | 4/2002 | Wysoki | |
| 2003/0004564 A1 | 1/2003 | Elkins et al. | |
| 2003/0191504 A1 | 10/2003 | Meadows et al. | |
| 2003/0212373 A1 * | 11/2003 | Hall | A61M 25/0668 604/263 |
| 2004/0064147 A1 * | 4/2004 | Struble | A61M 25/0668 606/129 |
| 2005/0090779 A1 | 4/2005 | Osypka | |
| 2005/0256541 A1 * | 11/2005 | Stypulkowski | A61N 1/08 607/3 |
| 2006/0217779 A1 | 9/2006 | Ransbury et al. | |
| 2007/0016089 A1 | 1/2007 | Fischell et al. | |
| 2007/0244407 A1 * | 10/2007 | Osorio | A61B 5/4094 600/544 |
| 2008/0249379 A1 | 10/2008 | Furman | |
| 2009/0076522 A1 | 3/2009 | Shan | |
| 2009/0192381 A1 * | 7/2009 | Brockway | A61N 1/0504 600/373 |
| 2010/0292532 A1 * | 11/2010 | Kadykowski | A61B 17/32 600/104 |
| 2011/0034876 A1 * | 2/2011 | Eversull | A61M 25/0668 604/172 |
| 2013/0018309 A1 * | 1/2013 | Ewing | A61M 25/001 604/103.05 |
| 2015/0133954 A1 * | 5/2015 | Seifert | A61B 17/3415 606/129 |

* cited by examiner

APPARATUS AND METHOD FOR IMPLANTING AN IMPLANTABLE DEVICE

TECHNICAL FIELD

The present patent document pertains generally to an insertion tool and more particularly, but not by way of limitation, to an insertion tool for subcutaneous placement of an implantable medical device.

BACKGROUND

Implantable devices that monitor cardiac physiologic activity are frequently implanted subcutaneously under a patient's skin in the chest. An implantable loop recorder (ILR) is an example of a device that may be implanted in this fashion.

To implant an ILR device with a flexible lead or antenna, an incision is made, a subcutaneous pocket is formed near the incision, and a tunnel is formed to extend away from the pocket for placement of the flexible lead using a surgical tool, such as forceps or scissors, or a finger. The ILR device can be inserted through the incision and placed in the subcutaneous pocket, tested for proper operation, and repositioned if necessary. The incision is then closed.

Implanting such ILR devices with flexible components in this manner may be difficult, especially for physicians who are not skilled in device implantation. If the ILR device is improperly implanted, undesirable complications for the patient, such as prolonged healing time, or suboptimal device performance may result. In addition, tearing of tissue during formation of the pocket and tunnel, for example, may result in tissue bleeding that requires appropriate steps during surgery to avoid hematoma. In addition, it may be necessary to employ fluoroscopy to assure that the antenna is properly positioned under the skin. If not properly positioned, the ILR and antenna may require repositioning to obtain an optimal ECG signal. This can extend the surgery duration, which can increase risk of infection and trauma, as well as expense.

OVERVIEW

This overview is intended to provide an overview of subject matter of the present patent application. It is not intended to provide an exclusive or exhaustive explanation of the invention. The detailed description is included to provide further information about the present patent application.

The present inventors have recognized, among other things, that the present subject matter can be used to subcutaneously implant a device. The present inventors have further recognized, among other things, that the present subject matter, in various examples, can provide a simpler approach to insertion, shorter insertion time, reduced risk of complications, reduced expense, and/or a reduced need for expensive equipment, such as fluoroscopy, during device placement. To better illustrate the apparatuses and methods described herein, a non-limiting list of examples is provided here:

Example 1 can include subject matter that can include an apparatus for subcutaneously inserting an implantable device within a patient. The implantable device includes a housing and an antenna. The antenna includes an antenna length. The apparatus includes a dilator portion including a dilator including a dilator length. The dilator portion is configured to separate tissue to create a subcutaneous pocket within the patient sized and shaped to accommodate the implantable device within the subcutaneous pocket. A sheath portion includes a sheath sized and shaped to accommodate the dilator within a sheath lumen. The sheath is configured to accommodate the antenna of the implantable device with the dilator removed from within the sheath, wherein the sheath includes a sheath length that is at least substantially as long as the antenna length. The sheath is configured to separate to allow removal of the sheath around the implantable device to remove the sheath from and leave the implantable device within the subcutaneous pocket within the patient.

In Example 2, the subject matter of Example 1 is optionally configured such that the dilator portion includes a handle configured to separate tissue to create the subcutaneous pocket, such that the dilator portion is configured to create a portion of the subcutaneous pocket configured to accommodate the antenna of the device. The handle is configured to create a portion of the subcutaneous pocket configured to accommodate the housing of the device.

In Example 3, the subject matter of any one of Examples 1-2 is optionally configured such that the sheath portion includes a sheath housing at a sheath proximal end, the sheath housing including a passage fluidly coupled with the sheath lumen.

In Example 4, the subject matter of Example 3 is optionally configured such that the dilator portion includes a handle, the handle having a portion complementary to the passage of the sheath housing to fit within the passage with the dilator disposed within the sheath.

In Example 5, the subject matter of any one of Examples 3-4 is optionally configured such that the passage of the sheath housing includes a funnel shape configured to facilitate insertion of the antenna within the sheath lumen.

In Example 6, the subject matter of any one of Examples 3-5 is optionally configured such that the sheath housing includes a first material and the sheath includes a second material, the first material being different than the second material.

In Example 7, the subject matter of any one of Examples 1-6 is optionally configured such that the dilator includes a distal dilator end including an atraumatic shape. The dilator length is longer than the sheath length to allow the distal dilator end to extend distally from the sheath.

In Example 8, the subject matter of Example 7 is optionally includes at least two electrodes configured to electrically couple to a test device. The electrodes are configured to verify a signal at a location within the patient prior to implantation of the implantable device.

In Example 9, the subject matter of any one of Examples 1-8 is optionally configured such that the sheath is configured to split with removal of the sheath over the implantable device.

In Example 10, the subject matter of Example 9 is optionally configured such that the sheath is configured to split substantially longitudinally along the sheath.

In Example 11, the subject matter of any one of Examples 1-10 is optionally configured such that the sheath includes a substantially longitudinal split extending from a proximal sheath end to a distal sheath end. The sheath is configured to spread apart along the split to allow removal of the sheath past the housing of the implantable device.

In Example 12, the subject matter of Example 11 is optionally configured such that the sheath includes a first edge and a second edge forming the substantially longitudinal split, the first edge being proximate the second edge.

In Example 13, the subject matter of Example 12 is optionally configured such that the first edge is separated from the second edge by a gap.

In Example 14, the subject matter of Example 12 is optionally configured such that the first edge abuts the second edge.

In Example 15, the subject matter of Example 12 is optionally configured such that the first edge overlaps the second edge.

Example 16 can include, or can optionally be combined with any one of Examples 1-15 to include subject matter that can include an apparatus for subcutaneously inserting an implantable device within a patient. The implantable device includes a housing and an antenna. The antenna includes an antenna length. The apparatus includes a dilator portion including a dilator including a dilator length. The dilator portion is configured to separate tissue to create a subcutaneous pocket within the patient sized and shaped to accommodate the implantable device within the subcutaneous pocket. A sheath portion includes a sheath is sized and shaped to accommodate the dilator within a sheath lumen. The sheath is configured to accommodate the antenna of the implantable device with the dilator removed from within the sheath, wherein the sheath includes a sheath length that is at least substantially as long as the antenna length. A sheath housing is disposed at a proximal sheath end. The sheath housing includes a passage fluidly coupled with the sheath lumen at a sheath housing distal end and extends through the sheath housing to a sheath housing proximal end. The sheath housing includes an opening in a sidewall of the sheath housing, wherein the sheath is configured to separate along a separation line substantially aligning with the opening in the sidewall of the sheath housing. The separation line and the opening cooperating to allow the housing to pass through the opening and the separated sheath with removal of the sheath from the implantable device to leave the implantable device within the subcutaneous pocket within the patient.

In Example 17, the subject matter of Example 16 is optionally configured such that the sheath is configured to split with removal of the sheath over the implantable device.

In Example 18, the subject matter of Example 16 is optionally configured such that the sheath includes a first edge and a second edge forming a substantially longitudinal split extending from a sheath proximal end to a sheath distal end, wherein the sheath is configured to spread apart along the split to allow removal of the sheath past the housing of the implantable device.

In Example 19, the subject matter of Example 18 is optionally configured such that the dilator portion includes a handle configured to separate tissue to create the subcutaneous pocket. The dilator portion is configured to create a portion of the subcutaneous pocket configured to accommodate the antenna of the device. The handle is configured to create a portion of the subcutaneous pocket configured to accommodate the housing of the device.

In Example 20, the subject matter of Example 18 optionally includes at least two electrodes configured to electrically couple to a test device. The electrodes are configured to verify a signal at a location within the patient prior to implantation of the implantable device.

DETAILED DESCRIPTION

The present patent application relates to apparatuses and methods for subcutaneous placement of an implantable medical device. In some examples, the present apparatuses and methods can be used for implanting a medical device, such as, but not limited to, an implantable loop recorder (ILR).

The present inventors have recognized, among other things, that the present subject matter can be used to subcutaneously implant a device. The present inventors have further recognized, among other things, that the present subject matter, in various examples, can provide a simpler approach to insertion, shorter insertion time, reduced risk of complications, reduced expense, and/or a reduced need for expensive equipment, such as fluoroscopy, during device placement. It should be understood, however, that the subject matter described herein can be used with other implantable medical devices and/or can be used in conjunction with an external device in some examples.

Figure 1:
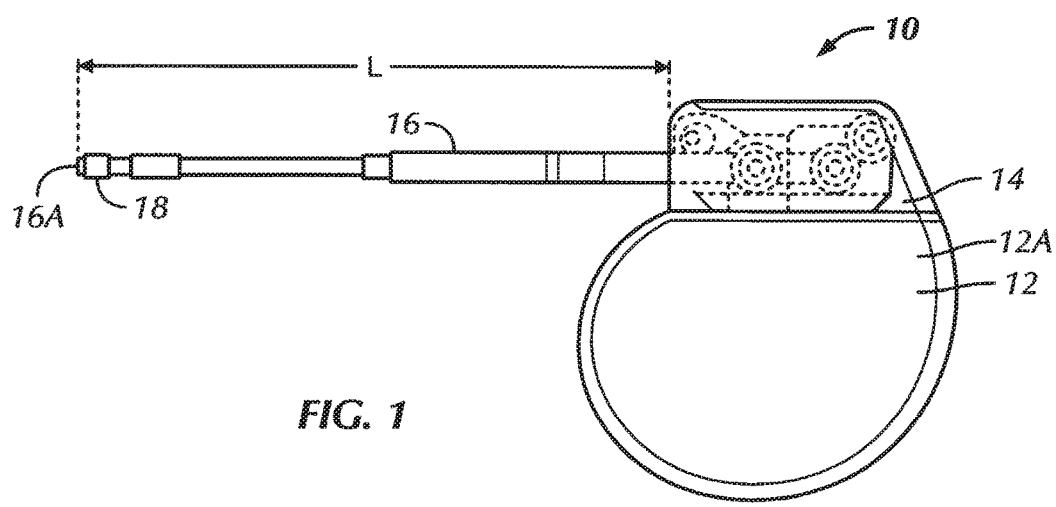
FIG. 1 shows an example implantable apparatus that can be implanted within a patient in accordance with at least one example of the invention.

Referring now FIG. 1, an exemplary implantable device 10, such as an implantable loop recorder (ILR), is shown, which can be subcutaneously implanted under a patient's skin. The ILR includes, in some examples, a housing 12, for instance, for device electronics and/or a battery power source. In some examples, a header 14 is supported on the housing and includes conductors connected to the device electronics through one or more hermetic feedthroughs. An antenna 16, in some examples, supporting a distal electrode 18 extends outwardly from the header 14 and has an antenna length L measured from the header 14 to a distal end 16A of the antenna 16. This device can be used, for instance, to record an electrocardiogram (ECG) signal for the patient.

In some examples, a first end of the flexible antenna 16 is attached at a fixation point to the header 14, and can generally flex or bend about the fixation point. The header 14 thus stabilizes the flexible antenna 16, yet allows it to bend and flex about the fixation point to conform to body tissue channel formation and subsequent tissue movement and flexing as the patient's muscles contract and expand during daily activities. In general, the flexible antenna 16 can bend at any appropriate angle with respect to the fixation point at the header 14, and in any appropriate direction.

The ILR device 10 can house a battery, which may be of a single-use or rechargeable chemistry, and circuitry (e.g., an electronics module) for performing actions consistent with the device's intended purpose. Without limitation, examples of actions that may be performed with some implementations of the device include measuring one or more physiologic signals, storing the measured signal(s) in memory within the device 10, processing collected data, wirelessly transmitting or receiving information to/from an external device, and others. In some examples, the housing 12 can include a charging coil that can be excited (e.g., with an external charging coil placed in proximity to the implant location) to recharge a rechargeable battery of the device.

In some examples, using one of the tunneling tools and techniques discussed herein, the ILR 10 can be implanted in a minimally invasive fashion that minimizes an incision size for insertion; minimizes trauma to body tissue during formation of a subdermal or subcutaneous channel for the implantable device 10; minimizes risk of puncture or intrusion upon a muscle layer, intercostal space, or body organ; and provides a fitted implant location closely tailored to actual device dimensions. Because incision size can be reduced as compared to previous implant techniques, a scar from the insertion may be less noticeable. Also, by forming an appropriately sized pocket for the implantable device 10, a risk of hematoma can be reduced. Further, the devices, systems, and techniques disclosed herein can significantly reduce the time required for implantation, and can mitigate the need for fluoroscopy, thereby reducing the cost associated with the implantation procedure. Moreover, the simplicity of the approach described here can make implantation feasible in a procedure room or doctor's office, and can provide for consistently safe and effective results when implanted by physicians who lack experience and skills in placing implantable devices. For at least these reasons, physicians may prefer the systems, devices, and techniques discussed herein when compared to presently available implant methods and devices.

By way of example, the device 10, in some examples, can be a minimally invasive implantable monitoring device that senses and records a physiologic parameter, such as electrical activity of the heart, within a body of a patient. In some examples, the device 10 can include an implantable monitoring device that senses and records a physiologic parameter, such as an electrocardiogram (ECG) signal, within the body of the patient and wirelessly transmits information associated with the physiologic parameter to an external device. Such a monitoring-only device that records cardiac electrical information can be implanted in a human patient for a relatively short period of time, such as a few months, for example. Other physiologic parameters or combinations of parameters, such as other electrical signals (e.g., EEG signal, EMG neural signal, bio-impedance signal), mechanical signals (e.g., blood pressure signal, blood flow signal), chemical signals (e.g., glucose), temperature, and the like can similarly be recorded by the device 10 in various examples.

In some examples, the device 10 can be relatively small and can be sized and shaped for convenient implantation within a body of a patient, such as at a subcutaneous implant site, for example, in a pectoral region of a human patient. A tunneling tool according to the present invention may be used to directly insert the ILR 10 to a subcutaneous implant location.

In some examples, the ILR device 10 can include one or more electrodes for electrically interfacing to surrounding tissue for the purpose of sensing electrical activity. In some examples, the device 10 includes two electrodes. For example, FIG. 1 shows an implantable device with an exterior surface of the housing 12 providing a proximal electrode 12A. A distal electrode 18 is located proximate the distal end 16A of the antenna 16. The implantable device, in some examples, can be programmed to measure a potential difference (e.g., a subcutaneous ECG signal) between the proximal and distal electrodes 12A, 18. The electrodes 12A, 18 are each near a longitudinal end of the device 10. This placement can maximize signal vector length of a measured physiologic signal. In general, measured amplitude of a sensed physiologic signal, such as an ECU signal, will vary with device placement and orientation within the patient. Sensed signal amplitude can also be related to separation distance between the measuring electrodes. Positioning the electrodes 12A, 18 near opposite ends of the device 10 can maximize the amplitude of the sensed physiologic signal for a given device length, which can lead to better measurement results. In other implementations, device 10 includes three or more electrodes.

In some examples, one of the electrodes can include an excitation electrode or combination excitation/sense electrodes. As an example, the device can measure a bio-impedance for diagnostic purposes by injecting a known current between the electrodes and measuring a resulting voltage there between two electrodes. In some examples, the electrodes can include a conductive material such as titanium.

Referring to FIGS. 2A-2G, in some examples, an apparatus 200 is configured for aiding in the subcutaneous implantation within a patient of a device, such as, but not limited to a medical device. In some examples, the apparatus 200 is configured to create a subcutaneous pocket or other space within the patient in order to implant a device, such as the device 10, within the patient. In some examples, the apparatus 200 can be used to assist in implantation of a device, such as the device 10.

In some examples, the apparatus 200 is configured to aid in implantation of an implantable device, such as the device 10. In some examples, the apparatus 200 includes a dilator portion 210 and a sheath portion 240. In some examples, the dilator portion 210 includes a dilator 212 terminating at a distal dilator end 212A. In some examples, the distal dilator end 212A includes an atraumatic tip or is otherwise shaped and/or configured to minimize tissue damage or other unwanted effects of using the apparatus 200 to create a subcutaneous pocket or channel in which to implant a device, such as the device 10. In some examples, the dilator portion 210 includes a handle 214 from which the dilator 212 extends. The dilator 212 includes a dilator length D. In some examples, the dilator portion 210 includes any polymer including, but not limited to, one or more of high density polyethylene, nylon, polypropylene, or the like. In some examples, the dilator portion 210 can include any metal including, but not limited to, one or more of titanium, stainless steel, gold, silver, or any other biologically safe and inert metal. In some examples, the dilator portion 210 includes more than one material, such as a combination of two or more polymers, a combination of two or more metals, or a combination of one or more polymers and one or more metals. In some examples, the dilator portion 210 includes a flexible or pliable material, for instance, to allow at least a portion of the dilator 212 to be shaped, bent, or otherwise configured to contour body geometry of the patient. Such a flexible dilator 212, in some examples, can allow for the apparatus 200 to faithfully adhere to anatomical needs and/or specifics of the patient in formation of the subdermal or subcutaneous pocket or channel for positioning of the device 10.

In some examples, the sheath portion 240 includes a sheath 242 sized and shaped to accommodate the dilator 212 within a sheath lumen 243. In some examples, the sheath 242 is configured to accommodate the antenna 16 of the implantable device 10 with the dilator 212 removed from within the sheath 242. In some examples, the sheath 242 includes a sheath length S that is at least substantially as long as the antenna length L. In some examples, the sheath 242 is configured to separate to allow removal of the sheath 242 around the implantable device 10 to remove the sheath 242 from and leave the implantable device 10 within the patient. In some examples, the sheath portion 240 includes a sheath housing 244 at a sheath proximal end 240A. The sheath housing 244, in some examples, includes a first material and the sheath 242 includes a second material. In some examples, the first material is more rigid than the second material. In other examples, the first material and the second material include substantially the same rigidity. In further examples, the sheath housing 244 and the sheath 242 are formed from the same material. In some examples, the first material can include any polymer including, but not limited to, one or more of high density polyethylene, nylon, polypropylene, or the like. In some examples, the first material can include any metal including, but not limited to, one or more of titanium, stainless steel, gold, silver, or any other biologically safe and inert metal. In some examples, the sheath housing 244 includes more than one material, such as a combination of two or more polymers, a combination of two or more metals, or a combination of one or more polymers and one or more metals. In some examples, the second material can include various polymers including, but not limited to, one or more of polytetrafluoroethylene (PTFE), fluorinated ethylene propylene (FEP), perfluoroalkoxy (PFA), or the like. In some examples, the sheath 242 includes more than one material, such as a combination of two or more polymers. In some examples, the sheath 242 can include a combination of materials combined in a way to confer properties to the sheath 242 to be advantageous for the particular use of the apparatus 200. For instance, in some examples, a material can be used for a dorsal side of the sheath 242 to facilitate blunt force tissue dissection, and another material can be used for a ventral side of the sheath 242 to increase localized suppleness for facilitating material slitting, for instance, when advancing the device 10 through the sheath 242. It is noted that the materials listed for the sheath 242 and the sheath housing 244 are merely exemplary and that other materials or combinations of materials not specifically listed are contemplated herein.

In some examples, the sheath housing 244 includes a passage 244C fluidly coupled with the sheath lumen 243. The passage 244C, in some examples, is fluidly coupled with the sheath lumen 243 at a sheath housing distal end 244B and extends through the sheath housing 244 from the sheath housing distal end 244B to a sheath housing proximal end 244A. In some examples, the passage 244C of the sheath housing 244 includes a channel-like configuration. In some examples, the channel-like configuration of the sheath housing 244 allows access to the passage 244C along one side of the sheath housing 244, as well as at either end of the sheath housing 244. In some examples, the sheath housing 244 is generally U-shaped, horseshoe-shaped, or the like when viewed from either end. That is, in some examples, the sheath housing 244 includes an opening in a sidewall of the sheath housing 244. In some examples, the sheath 242 is configured to separate along a separation line substantially aligning with the opening in the sidewall of the sheath housing 244. In some examples, the separation line and the opening cooperate to allow the housing 12 to pass through the opening and the separated sheath 242 with removal of the sheath 242 from the implantable device 10.

Figure 2A:
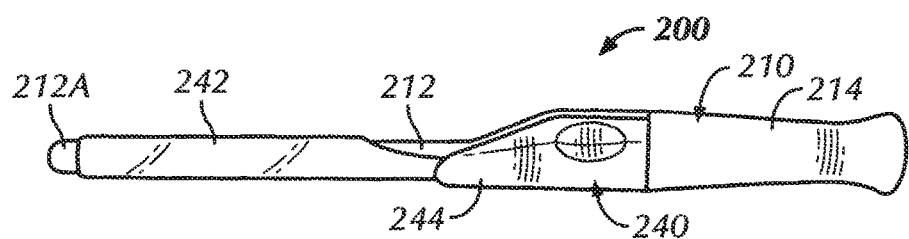
FIGS. 2A-2G show an apparatus for subcutaneously inserting an implantable device within a patient in accordance with at least one example of the invention.

In some examples, the dilator portion 210 and the sheath portion 240 are configured such that the dilator portion 210 and the sheath portion 240 selectively couple together, as shown in FIG. 2A. In some examples, the handle 214 includes a portion complementary to the passage 244C of the sheath housing 244 to fit within the passage 244C with the dilator 212 disposed within the sheath 242. In some examples, the dilator portion 210 and the sheath portion 240 are frictionally coupled together, such that the dilator portion 210 and the sheath portion 240 can be selectively uncoupled by a physician or other caregiver using the apparatus 200. In some examples, the dilator portion 210 and the sheath portion 240 include a detent or the like to inhibit unexpected uncoupling of the dilator portion 210 and the sheath portion 240.

Figure 2B:
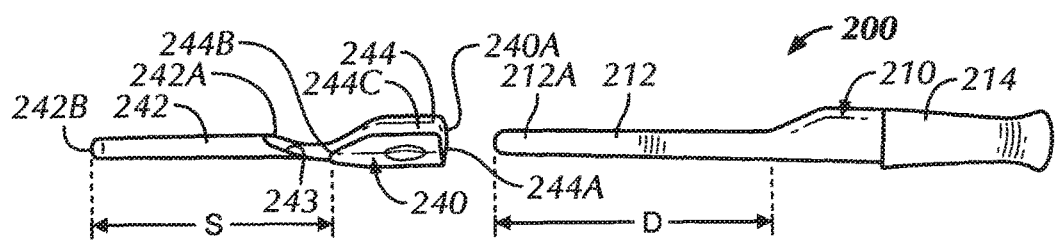

In some examples, with the dilator portion 210 and the sheath portion 240 coupled together, the distal dilator end 212A of the dilator 212 extends distally from the sheath 242. In some examples, the distal dilator end 212A includes an atraumatic shape to allow for tunneling or otherwise inserting the apparatus 200 within the patient with little to no tissue damage or other trauma. That is, in some examples, the dilator length D is longer than the sheath length S. In some examples, the dilator length D is longer than the sheath length S to allow the distal dilator end 212A to extend distally from the sheath 242. In some examples, the dilator 212 and the distal dilator end 212A facilitate tissue separation, tunneling, and/or placement of the apparatus 200 within and with respect to a patient. Once the apparatus 200 is positioned with respect to the patient, the dilator portion 210 can be removed from the sheath portion 240, leaving the sheath portion 240 in place with respect to the patient, as shown in FIG. 2B.

With the sheath portion 240 in place with respect to the patient, in some examples, an object, such as, for instance, the implantable device 10, can be passed through the sheath portion 240 to implant or partially implant the implantable device 10 or other object within the patient. In some examples, the antenna 16 can be passed through the passage 244C of the sheath housing 244 and into the sheath lumen 243. In some examples, the sheath housing 244 and/or the passage 244C of the sheath housing 244 includes a tapered or funnel-like configuration to facilitate insertion of the antenna 16 within the passage 244C and the sheath 242. In some examples, the passage 244C of the sheath housing 244 includes a funnel shape configured to facilitate insertion of the antenna 16 within the sheath lumen 243. In some examples, the sheath 242 creates a tunnel within the patient to allow placement of the antenna 16 within the patient without resistance or with decreased resistance, for instance, from tissue of the patient through and/or within which the implantable device 10 is being implanted. In this way, kinking, bending, or other misshaping of the antenna 16 can be minimized if not eliminated, which can lead to improved performance of the implantable device 10.

Because, in some examples, the housing 12 and/or the header 14 of the implantable device 10 is larger than the sheath lumen 243, the sheath 242 is configured to allow removal of the sheath 242 from within the patient and past the housing 12. In some examples, referring to FIGS. 2C, 2D, and 2G, the sheath 242 is splittable. In some examples, the sheath 242 is configured to split with removal of the sheath 242 over the implantable device 10. That is, in some examples, the sheath 242 is configured to split, rip, or otherwise separate from a proximal sheath end 242A to a distal sheath end 242B to allow the sheath portion 240 to be removed proximally from the patient around the housing 12 of the implantable device 10. In some examples, the sheath 242 is configured to split substantially longitudinally along the sheath 242.

Figure 2C:
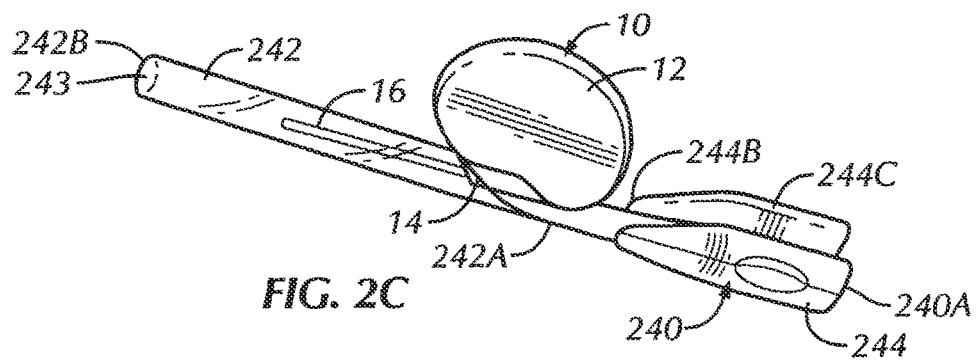
Figure 2D:
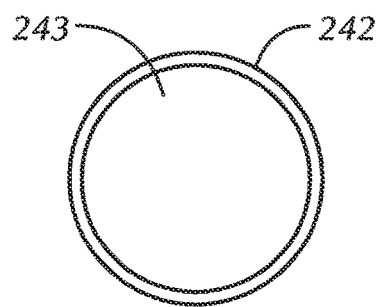
Figure 2E:
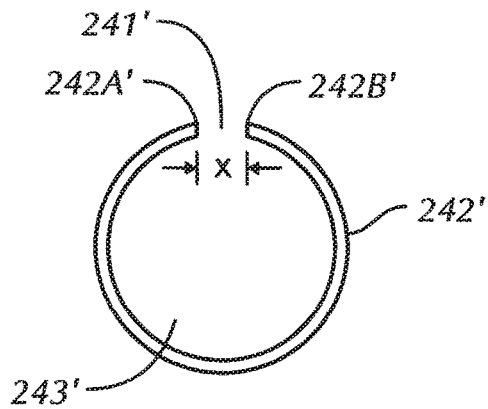
Figure 2F:
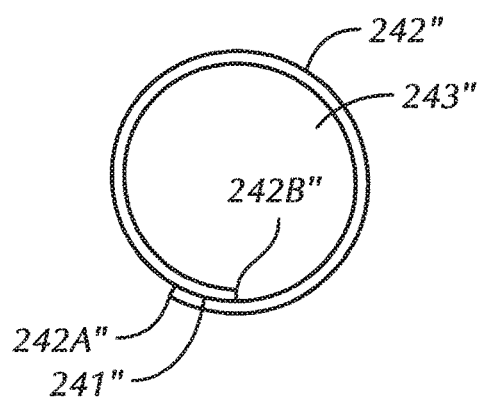
Figure 2G:
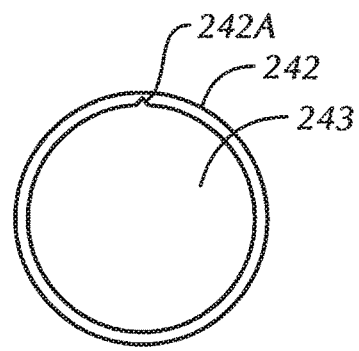

In some examples, referring specifically to FIG. 2G, the sheath 242 includes one or more score lines 242A to facilitate separation of the sheath 242. Although shown in FIG. 2G with only one score line 242A, it is contemplated that the sheath 242 includes more than one score line 242A. In some examples, the sheath includes two diametrically opposed score lines to facilitate the sheath splitting in half. In other examples, the sheath includes more than two score lines.

In some examples, the one or more score lines 242A are formed on an inside surface of the sheath 242, as shown in FIG. 2G. In other examples, the one or more score lines are formed on an outside surface of the sheath. In still other examples, the one or more score lines are formed on both an inside surface and an outside surface of the sheath.

In some examples, the one or more score lines 242A include a notch-shaped or v-shaped cut in the sheath 242. In some examples, the one or more score lines include a rounded cut in the sheath. In various examples, the one or more score lines include a thinned portion of the sheath to facilitate splitting of the sheath, along the one or more score lines. In some examples, the one or more score lines include a line of discrete thinned sections forming one or more perforated score lines.

In some examples, the one or more thinned areas or score lines 242A are mechanically formed in the sheath 242 using a cutting device, such as, but not limited to one or more of a stationary blade, an oscillating blade, a rotary cutter, a fluid cutter, a laser cutter, or the like. In some examples, the one or more thinned areas or score lines 242A are crimped into the sheath 242. In some examples, the one or more thinned areas or score lines 242A are molded in the sheath 242. In some examples, the one or more thinned areas or score lines 242A are formed in the sheath 242 through extrusion. Although several examples of forming the one or more thinned areas or score lines 242A are described herein, it should be understood that other ways of forming the one or more thinned areas or score lines 242A are contemplated herein.

In further examples, referring to FIG. 2E, sheath 242' is presplit. It should be understood that, in some examples, the apparatus 200 can include the presplit sheath 242' instead of the splittable sheath 242 described above. In some examples, the sheath 242' includes a substantially longitudinal split 241' extending from a sheath proximal end to a sheath distal end. In some examples, the sheath 242' is configured to spread apart along the split 241' to allow removal of the sheath 242' past the housing 12 of the implantable device 10. In some examples, the sheath 242' includes a first edge 242A' and a second edge 242B' forming the substantially longitudinal split 241', the first edge 242A' being proximate the second edge 242B'. In some examples, the first edge 242A' is separated from the second edge 242B' by a gap X. In other examples, the first edge 242A' abuts the second edge 242B'. In either case, the split 241' allows the sheath 242' to be removed from within the patient with at least a portion of the implantable device 10 extending out from within a lumen 243' of the sheath 242'.

In still other examples, referring to FIG. 2F, sheath 242" is presplit. It should be understood that, in some examples, the apparatus 200 can include the presplit sheath 242" instead of the splittable sheath 242 or the presplit sheath 242' described above. In some examples, the sheath 242" includes a substantially longitudinal split 241" extending from a sheath proximal end to a sheath distal end. In some examples, the sheath 242" is configured to spread apart along the split 241" to allow removal of the sheath 242" past the housing 12 of the implantable device 10. In some examples, the sheath 242" includes a first edge 242A" and a second edge 242B" forming the substantially longitudinal split 241", the first edge 242A" being proximate the second edge 242B". In some examples, the first edge 242A" overlaps the second edge 242B". In this way, the split 241" allows the sheath 242" to be removed from within the patient with at least a portion of the implantable device 10 extending out from within a lumen 243" of the sheath 242".

Still referring to FIGS. 2A-2G, in use, in some examples, the apparatus 200 (FIG. 2A) is used to create a pocket within the patient for placement of the device 10 within the patient. Once the pocket is created, in some examples, the dilator portion 210 is removed from the sheath portion 240 (FIG. 2B), leaving the sheath portion 240 in place within the patient. In some examples, the device 10 can then be at least partially placed within the sheath 242, 242', 242". For instance, in some examples, the antenna 16 of the device 10 can be inserted within the passage 244C and advanced into the lumen 243, 243', 243" of the sheath 242, 242', 242" (FIG. 2C). The sheath portion 240, in some examples, can then be pulled proximally out of the patient, around the housing 12 and the header 14 of the device 10 to remove the sheath portion 240 from within the patient while leaving the device 10 in place within the patient. In some examples, the sheath 242 is splittable (FIG. 2D or 2G) such that the sheath 242 splits, tears, or otherwise separates along a separation line with movement of the sheath 242 past the header 14 and/or the housing 12 of the device 10. In other examples, the sheath 242', 242" is presplit (FIGS. 2E and 2F) such that the sheath 242', 242" can be passed by the header 14 and/or the housing 12 of the device 10 during removal of the sheath portion 240 with the header 14 and/or the housing 12 of the device 10 passing through the split 241', 241" of the sheath 242', 242". In this way, the apparatus 200 can be used to create the pocket within the patient and assist in placing the device 10 within the patient. By creating the pocket and inserting the antenna 16 of the device using the sheath 242, 242', 242", the likelihood of the antenna 16 kinking, bending, or folding is decreased over insertion of the device 10 without the use of the apparatus 200.

Figure 3A:
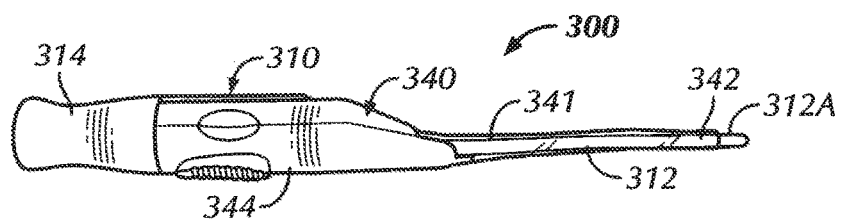
FIGS. 3A-3C show an apparatus for subcutaneously inserting an implantable device within a patient in accordance with at least one example of the invention.
Figure 3B:
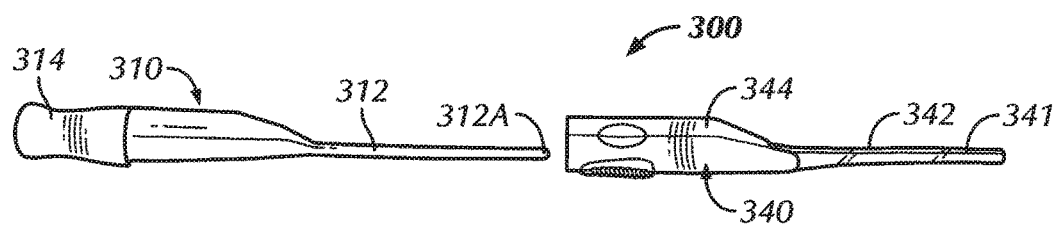
Figure 3C:
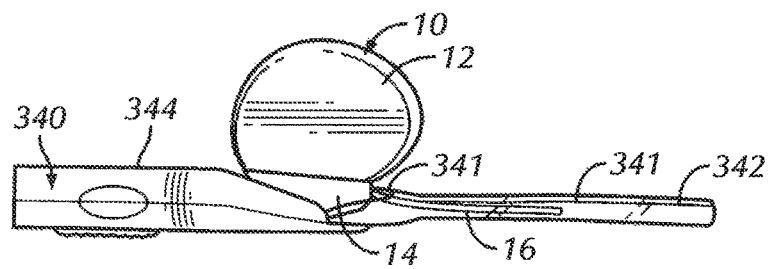

Referring to FIGS. 3A-3C, an apparatus 300 similar to the apparatus 200 is configured for aiding in the subcutaneous implantation within a patient of a device, such as, but not limited to a medical device. In some examples, the apparatus 300 is configured to create a subcutaneous pocket or other space within the patient in order to implant a device, such as the device 10, within the patient. In some examples, the apparatus 300 can be used to assist in implantation of a device, such as the device 10.

In some examples, the apparatus 300 includes a dilator portion 310 and a sheath portion 340. The dilator portion 310 and the sheath portion 340, in some examples, are configured such that the dilator portion 310 and the sheath portion 340 selectively couple together, as shown in FIG. 3A. In some examples, a handle 314 includes a portion complementary to a passage (for instance, similar to the passage 244C shown and described herein) of a sheath housing 344 to fit within the passage with a dilator 312 disposed within a sheath 342. In some examples, the sheath housing 344 and/or the passage of the sheath housing 344 includes a funnel-like configuration to facilitate insertion of the antenna 16 within the passage and the sheath 342. In some examples, the passage of the sheath housing 344 includes a funnel shape configured to facilitate insertion of the antenna 16 within a sheath lumen.

In some examples, the dilator portion 310 and the sheath portion 340 are frictionally coupled together, such that the dilator portion 310 and the sheath portion 340 can be selectively uncoupled by a physician or other caregiver using the apparatus 300. In some examples, the dilator portion 310 and the sheath portion 340 include a detent or the like to inhibit unexpected uncoupling of the dilator portion 310 and the sheath portion 340.

In some examples, the dilator 312 terminates at a distal dilator end 312A. In some examples, the distal dilator end 312A includes an atraumatic tip or is otherwise shaped and/or configured to minimize tissue damage or other unwanted effects of using the apparatus 300 to create a subcutaneous pocket in which to implant a device, such as the device 10. In some examples, the dilator 312 is sized to extend distally from the sheath 342 with the dilator portion 310 and the sheath portion 340 coupled together.

In some examples, the sheath 342 is presplit. It should be understood that, in some examples, the apparatus 300 can include the presplit sheath 342 or a splittable sheath similar to the splittable sheath 242 described and shown herein. In some examples, the sheath 342 includes a substantially longitudinal split 341 extending from a sheath proximal end to a sheath distal end. In some examples, the sheath 342 is configured to spread apart along the split 341 to allow removal of the sheath 342 past the housing 12 of the implantable device 10, as shown in FIG. 3C. In some examples, the sheath 342 is separated along the longitudinal split 341 by the header 14 and/or the housing 12 of the device 10 to allow removal of the sheath portion 340 from the patient while maintaining the device 10 in place within the patient. That is, the split 341 allows the sheath 342 to be removed from within the patient with at least a portion of the implantable device 10 extending out from within the lumen of the sheath 342. In various examples, the presplit sheath 342 can include a longitudinal split 341 formed by abutting edges, separated edges, or overlapping edges, similar to the examples described and shown herein with respect to the apparatus 200.

Still referring to FIGS. 3A-3C, in use, in some examples, the apparatus 300 (FIG. 3A) is used to create a pocket within the patient for placement of the device 10 within the patient. Once the pocket is created, in some examples, the dilator portion 310 is removed from the sheath portion 340 (FIG. 3B), leaving the sheath portion 340 in place within the patient. In some examples, the device 10 can then be at least partially placed within the sheath 342. For instance, in some examples, the antenna 16 of the device 10 can be inserted within the passage of the sheath portion 340 and advanced into the lumen of the sheath 342 (FIG. 3C). The sheath portion 340, in some examples, can then be pulled proximally out of the patient, around the housing 12 and the header 14 of the device 10 to remove the sheath portion 340 from within the patient while leaving the device 10 in place within the patient. In some examples, the sheath 342 is presplit such that the sheath 342 can be passed by the header 14 and/or the housing 12 of the device 10 during removal of the sheath portion 340 with the header 14 and/or the housing 12 of the device 10 passing through the split 341 of the sheath 342. In this way, the apparatus 300 can be used to create the pocket within the patient and assist in placing the device 10 within the patient. By creating the pocket and inserting the antenna 16 of the device using the sheath 342, the likelihood of the antenna 16 kinking, bending, or folding is decreased over insertion of the device 10 without the use of the apparatus 300.

Referring to FIGS. 4A-4D, in some examples, an apparatus 400 is configured for aiding in the subcutaneous implantation within a patient of a device, such as, but not limited to a medical device. In some examples, the apparatus 400 is configured to create a subcutaneous pocket or other space within the patient in order to implant a device, such as the device 10, within the patient. In some examples, the apparatus 400 can be used to assist in implantation of a device, such as the device 10.

Figure 4A:
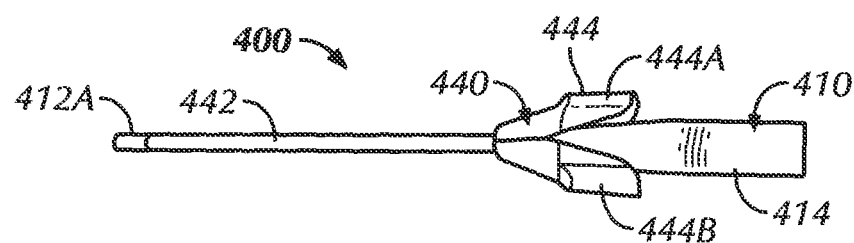
FIGS. 4A-4D show an apparatus for subcutaneously inserting an implantable device within a patient in accordance with at least one example of the invention.
Figure 4B:
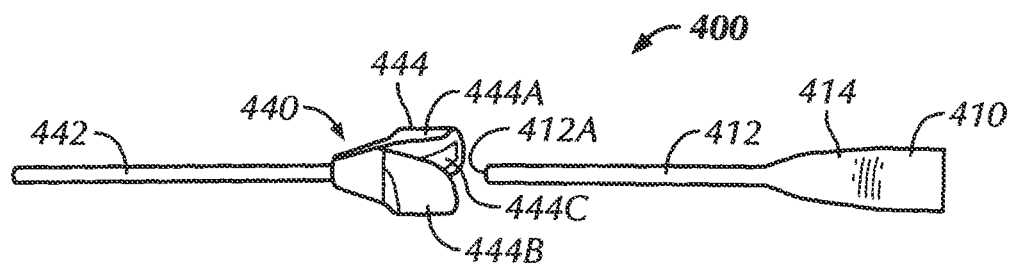

In some examples, the apparatus 400 includes a dilator portion 410 and a sheath portion 440. The dilator portion 410 and the sheath portion 440, in some examples, are configured such that the dilator portion 410 and the sheath portion 440 selectively couple together, as shown in FIG. 4A. In some examples, a handle 414 of the dilator portion 410 includes a portion complementary to a passage 444C of a sheath housing 444 to fit within the passage 444C with a dilator 412 disposed within a sheath 442. In some examples, the sheath 442 is attached to the sheath housing 444. In some examples, the sheath housing 444 and/or the passage 444C of the sheath housing 444 includes a funnel-like configuration to facilitate insertion of the antenna 16 within the passage and the sheath 442. In some examples, the passage of the sheath housing 444 includes a funnel shape configured to facilitate insertion of the antenna 16 within a sheath lumen. In some examples, the sheath housing 444 includes two housing portions 444A, 444B that form the passage 444C. In some examples, the sheath housing 444 can include more than two housing portions. The housing portions 444A, 444B, in some examples, are configured to separate, for instance, to allow the sheath portion 440 to be removed around the housing 12 and/or the header 14 of the device 10, as is described in more detail below.

In some examples, the dilator portion 410 and the sheath portion 440 are frictionally coupled together, such that the dilator portion 410 and the sheath portion 440 can be selectively uncoupled by a physician or other caregiver using the apparatus 400. In some examples, the dilator portion 410 and the sheath portion 440 include a detent or the like to inhibit unexpected uncoupling of the dilator portion 410 and the sheath portion 440.

In some examples, the dilator 412 terminates at a distal dilator end 412A. In some examples, the distal dilator end 412A includes an atraumatic tip or is otherwise shaped and/or configured to minimize tissue damage or other unwanted effects of using the apparatus 400 to create a subcutaneous pocket in which to implant a device, such as the device 10. In some examples, the dilator 412 is sized to extend distally from the sheath 442 with the dilator portion 410 and the sheath portion 440 coupled together.

Figure 4C:
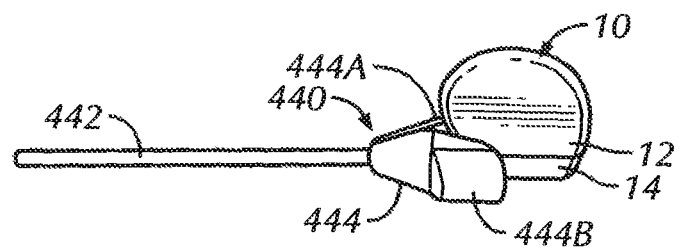
Figure 4D:
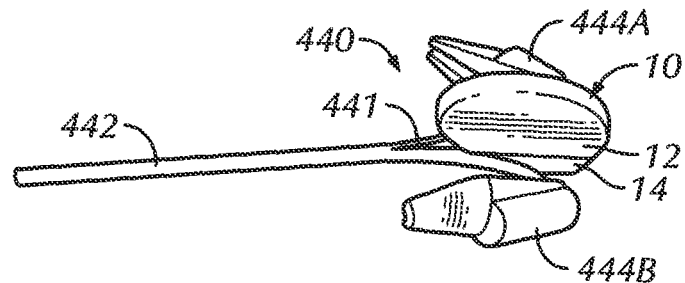

In some examples, the sheath 442 is splittable. It should be understood that, in some examples, the apparatus 400 can include the splittable sheath 442 (similar to the splittable sheathes 242 described and shown herein) or a presplit sheath (similar to the presplit sheathes 242', 242", 342 described and shown herein). In some examples, once the apparatus 400 is positioned as desired with respect to the patient, the dilator portion 410 is removed (FIG. 4B) and the antenna of the device 10 is inserted within the passage 444C (FIG. 4C). When it is desired to remove the sheath portion 440 from within the patient, in some examples, the housing portions 444A, 444B can be separated and the sheath 442 can be split to allow passage of the sheath housing 444 around the device 10 in order to remove the sheath housing 444 from the patient while leaving the device 10 in place within the patient. In some examples, the housing portions 444A, 444B of the sheath housing 444 are molded together with a frangible connection that can be broken when it is desired to separate the housing portions 444A, 444B from one another. In some examples, the housing portions 444A, 444B are frictionally engaged with one another, the housing portions 444A, 444B being able to be disengaged from one another by the physician or other caregiver in order to separate the housing portions 444A, 444B from one another. In some examples, the housing portions 444A, 444B are engaged with one another using one or more of a tab-in-slot configuration, a detent configuration, a sliding engagement configuration, or the like. With the housing portions 444A, 444B separated, in some examples, the sheath 442 can then be split (FIG. 4D) in order to remove the sheath 442 from within the patient while leaving the device 10 in place within the patient. In some examples, the separated housing portions 444A, 444B can be pulled apart to split the sheath 442. In some examples, the sheath 442 is attached to proximal ends of the housing portions 444A, 444B, as shown in FIG. 4D. In other examples, the sheath 442 can be attached to distal ends of the housing portions 444A, 444B or at locations intermediate the proximal ends and distal ends of the housing portions 444A, 444B. In some examples, the housing 12 and/or the header 14 of the device 10 is used to split the sheath 442 as the sheath 442 is moved past the housing 12 and the header 14 of the device 10, either in addition to or instead of pulling apart of the housing portions 444A, 444B. In some examples, the sheath 442 includes a split 441 that extends along the length of the sheath 442 with separation of the housing portions 444A, 444B and/or moving of the sheath 442 past the header 14 and/or housing 12 of the device 10. In some examples, the split 441 propagates from a proximal end of the sheath 442 to a distal end of the sheath 442 to allow the sheath portion 440 to be removed from the patient around the device 10 while leaving the device 10 in place within the patient. In some examples, the sheath 442 includes a second split (not visible in FIG. 4D), such that the sheath 442 can be split into two pieces, with one piece attached to one housing portion 444A and another piece attached to the other housing portion 444B, with removal of the sheath portion 440 around the device 10. In other examples, the sheath 442 can be configured to separate along a single split 441 in order to remove the sheath portion 440 from within the patient.

Referring to FIGS. 5A-5E, in some examples, an apparatus 500 is configured for aiding in the subcutaneous implantation within a patient of a device, such as, but not limited to a medical device. In some examples, the apparatus 500 is configured to create a subcutaneous pocket or other space within the patient in order to implant a device, such as the device 10, within the patient. In some examples, the apparatus 500 can be used to assist in implantation of a device, such as the device 10.

Figure 5A:
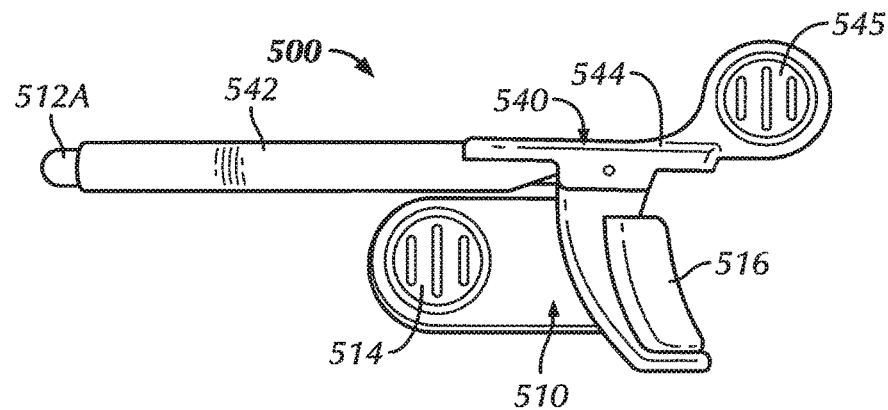
FIGS. 5A-5E show an apparatus for subcutaneously inserting an implantable device within a patient in accordance with at least one example of the invention.
Figure 5B:
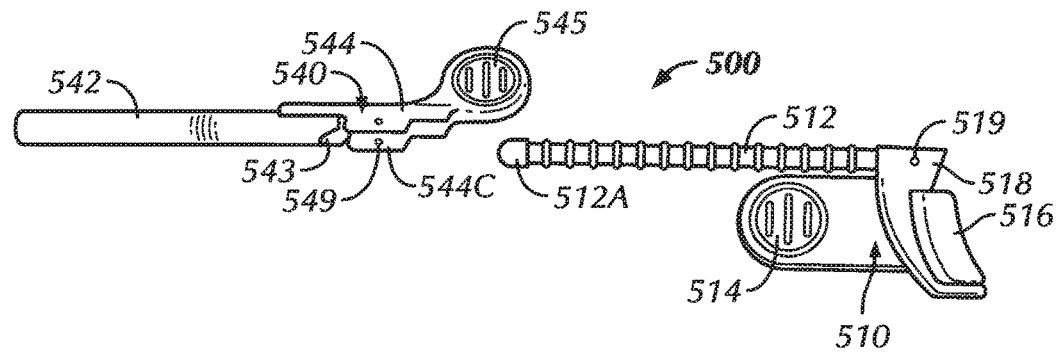

In some examples, the apparatus 500 includes a dilator portion 510 and a sheath portion 540. The dilator portion 510 and the sheath portion 540, in some examples, are configured such that the dilator portion 510 and the sheath portion 540 selectively couple together, as shown in FIG. 5A. In some examples, a handle 514 includes a portion 518 complementary to a passage 544C of a sheath housing 544 to fit within the passage 544C with a dilator 512 disposed within a sheath 542. In some examples, the handle 514 is shaped and sized to approximate the size of the housing 12 of the device 10, such that with advancement of at least a portion of the handle 514 into the patient through an incision creates a subcutaneous or subdermal pocket substantially sized to accommodate the housing 12 of the device 10 within the pocket. In this way, insertion of the apparatus 500 at least partially within the patient creates a tunnel (for instance, for the antenna 16 of the device) using the dilator 512 and a pocket (for instance, for the housing 12 of the device 10) using the handle 514. In this way, in some examples, a pocket sized more accurately to the size of the housing 12 of the device 10 can be created, thereby decreasing the possibility of creating an improperly-sized pocket, as is possible when creating the pocket without using a guide. Use of the handle 514 to size the pocket can decrease, if not eliminate, creation of an improperly-sized pocket for the housing 12 of the device 10 and decrease, if not eliminate, issues associated with an improperly-sized pocket. For instance, too large of a pocket would allow migration of the housing 12 and the device 10 within the body, whereas too small of a pocket would require one or more subsequent attempts to enlarge the pocket, which increases procedure time and expense.

In some examples, the sheath housing 544 and/or the passage of the sheath housing 544 includes a funnel-like configuration to facilitate insertion of the antenna 16 within the passage and the sheath 542. In some examples, the passage of the sheath housing 544 includes a funnel shape configured to facilitate insertion of the antenna 16 within a sheath lumen 543. In some examples, the sheath portion 540 includes a sheath handle 545 or other gripping portion to facilitate grasping, handling, maneuvering, and the like of the sheath portion 540 during use of the sheath portion 540 by the physician or other caregiver.

In some examples, the dilator portion 510 and the sheath portion 540 are frictionally coupled together, such that the dilator portion 510 and the sheath portion 540 can be selectively uncoupled by a physician or other caregiver using the apparatus 500. In some examples, the dilator portion 510 and the sheath portion 540 include a detent configuration or the like to inhibit unexpected uncoupling of the dilator portion 510 and the sheath portion 540. In some examples, the dilator portion 510 includes one or more protrusions 519 that interact with one or more dimples 549 of the sheath portion 540 to inhibit unexpected uncoupling of the dilator portion 510 and the sheath portion 540. In other examples, other connection configurations are contemplated, such as, but not limited to, one or more of a tab-in-slot configuration, a slidable rail-in-slot configuration, or the like.

In some examples, the dilator 512 terminates at a distal dilator end 512A. In some examples, the distal dilator end 512A includes an atraumatic tip or is otherwise shaped and/or configured to minimize tissue damage or other unwanted effects of using the apparatus 500 to create a subcutaneous pocket in which to implant a device, such as the device 10. In some examples, the dilator 512 is sized to extend distally from the sheath 542 with the dilator portion 510 and the sheath portion 540 coupled together.

Figure 5C:
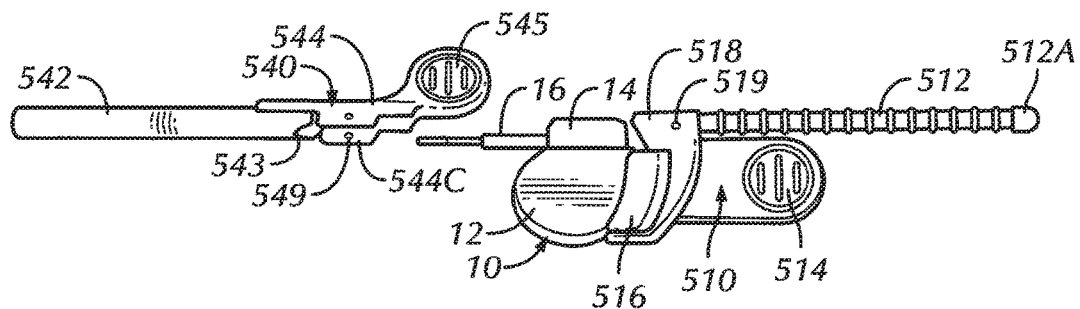
Figure 5D:
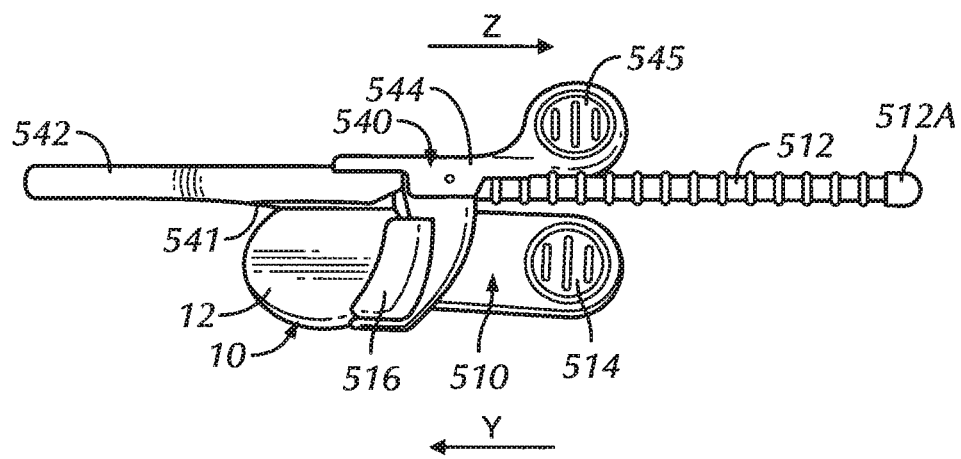
Figure 5E:
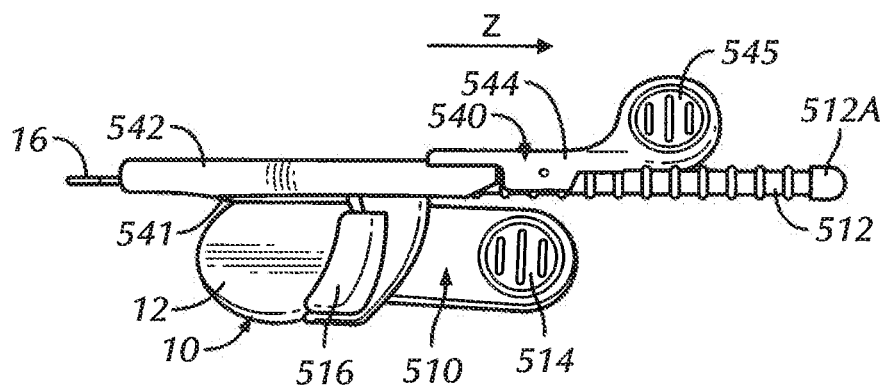

In some examples, because the housing 12 and/or header 14 of the implantable device 10 is larger than the sheath lumen 543, the sheath 542 is configured to allow removal of the sheath 542 from within the patient and past the housing 12 and/or header 14. In some examples, the sheath 542 is splittable with removing of the sheath portion 540 past the device 10 (similar to the splittable sheathes 242 described and shown herein). In some examples, pulling the sheath 542 past the housing 12 and/or the header 14 of the device 10 separates the sheath 542 and causes a split 541 to propagate along the sheath 542, as seen in FIGS. 5D and 5E. In some examples, the sheath 542 is configured to split, rip, or otherwise separate from a proximal sheath end to a distal sheath end to allow the sheath portion 540 to be removed proximally from the patient around the housing 12 and/or the header 14 of the implantable device 10. In some examples, the sheath 542 is configured to split substantially longitudinally along the sheath 542. In some examples, it is contemplated that the sheath 542 is presplit in a manner similar to that described above with respect to the presplit sheathes 242', 242", 342 described and shown herein.

In some examples, the dilator portion 510 includes a receptacle 516 or other surface for interacting with the device 10 to abut at least a portion of the device 10 and aid in pushing the device into the sheath portion 510 and/or the patient and/or holding the device 10 in place within the patient during removal of the sheath portion 540 from the patient. That is, in some examples, once the apparatus 500 is in place within the patient so that a tunnel is created by the dilator 512 for the antenna 16 and a pocket is created by the handle 514 for the housing 12, the dilator portion 510 can be removed from the sheath portion 540 (FIG. 5B), leaving the sheath portion 540 within the patient. The device 10, in some examples, can then be placed within the receptacle 516 or otherwise against a surface of the dilator portion. In some examples, the dilator portion 510 is rotated 180 degrees so that the dilator 512 extends generally proximally and the receptacle 516 or other surface for interacting with the device 10 faces generally distally to accept, abut, or otherwise interact with the device 10 (FIG. 5C). The antenna 16 of the device 10, in some examples, can then be inserted within the passage 544C and/or the lumen 543 of the sheath 542 and the device 10 can be pushed distally into the sheath 542 and into place in the tunnel and pocket within the patient by distally pushing the dilator portion 510 in the direction of arrow Y (FIG. 5D). In some examples, the dilator portion 510, with the receptacle 516 or other surface accepting, abutting, or otherwise interacting with the device 10, can be held to maintain placement of the device 10 within the patient during removal of the sheath portion 540 from within the patient and around the header 14 and/or the housing 12 of the device 10. In some examples, the sheath portion 540 can be removed from within the patient by grasping the sheath handle 545 and pulling the sheath portion 540 proximally over and past the device 10 and the dilator portion 510 in the direction of arrow Z (FIGS. 5D and 5E). Once the sheath portion 540 is removed from within the patient, in some examples, the dilator portion 510 can be removed from engagement, abutment, or other interaction with the device 10, leaving the device 10 in place within the patient. It is noted that in some examples, the dilator 512 and/or the handle 514 of the dilator portion 510 can be grasped by the physician or other caregiver in order to manipulate and/or push the device 10 distally into place and/or hold the device 10 during removal of the sheath portion 540 from within the patient. In other examples, the device 10 can be placed within the patient and held in place during removal of the sheath portion 540 from the patient without using the dilator portion 510 and or the receptacle 516 of the dilator portion 510.

Figure 6A:
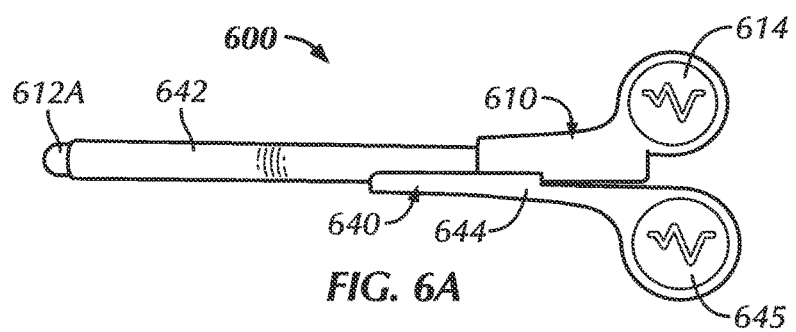
FIGS. 6A-6C show an apparatus for subcutaneously inserting an implantable device within a patient in accordance with at least one example of the invention.
Figure 6B:
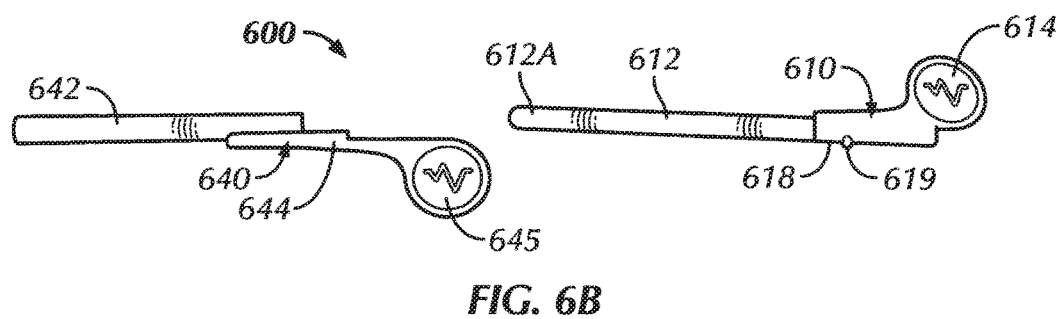
Figure 6C:
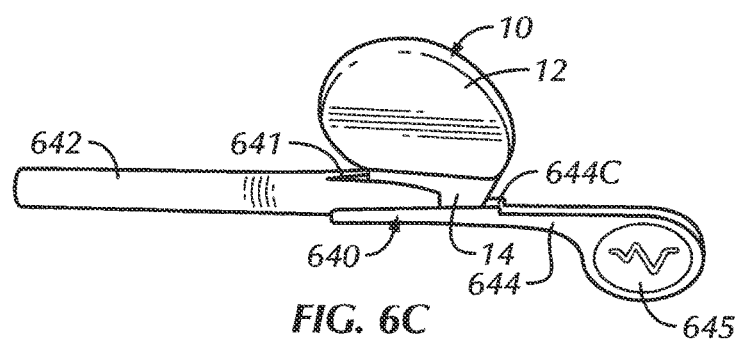

Referring to FIGS. 6A-6C, in some examples, an apparatus 600 is configured for aiding in the subcutaneous implantation within a patient of a device, such as, but not limited to a medical device. In some examples, the apparatus 600 is configured to create a subcutaneous pocket or other space within the patient in order to implant a device, such as the device 10, within the patient. In some examples, the apparatus 600 can be used to assist in implantation of a device, such as the device 10.

In some examples, the apparatus 600 includes a dilator portion 610 and a sheath portion 640. The dilator portion 610 and the sheath portion 640, in some examples, are configured such that the dilator portion 610 and the sheath portion 640 selectively couple together, as shown in FIG. 6A. In some examples, a handle 614 includes a portion 618 complementary to a passage 644C of a sheath housing 644 to fit within the passage 644C with a dilator 612 disposed within a sheath 642. In some examples, the sheath housing 644 and/or the passage of the sheath housing 644 includes a funnel-like configuration to facilitate insertion of the antenna 16 of the device 10 within the passage and the sheath 642. In some examples, the passage of the sheath housing 644 includes a funnel shape configured to facilitate insertion of the antenna 16 within a sheath lumen. In some examples, the sheath portion 640 includes a sheath handle 645 or other gripping portion to facilitate grasping, handling, maneuvering, and the like of the sheath portion 640 during use of the sheath portion 640 by the physician or other caregiver.

In some examples, the dilator portion 610 and the sheath portion 640 are frictionally coupled together, such that the dilator portion 610 and the sheath portion 640 can be selectively uncoupled by a physician or other caregiver using the apparatus 600. In some examples, the dilator portion 610 and the sheath portion 640 include a detent configuration or the like to inhibit unexpected uncoupling of the dilator portion 610 and the sheath portion 640. In some examples, the dilator portion 610 includes one or more protrusions 619 that interact with one or more dimples of the sheath portion 640 to inhibit unexpected uncoupling of the dilator portion 610 and the sheath portion 640. In other examples, other connection configurations are contemplated, such as, but not limited to, one or more of a tab-in-slot configuration, a slidable rail-in-slot configuration, or the like.

In some examples, the dilator 612 terminates at a distal dilator end 612A. In some examples, the distal dilator end 612A includes an atraumatic tip or is otherwise shaped and/or configured to minimize tissue damage or other unwanted effects of using the apparatus 600 to create a subcutaneous pocket in which to implant a device, such as the device 10. In some examples, the dilator 612 is sized to extend distally from the sheath 642 with the dilator portion 610 and the sheath portion 640 coupled together.

Because, in some examples, the housing 12 and/or the header 14 of the implantable device 10 is larger than the sheath lumen, the sheath 642 is configured to allow removal of the sheath 642 from within the patient and past the housing 12 and/or header 14. In some examples, the sheath 642 is splittable with removing of the sheath portion 640 past the device 10 (similar to the splittable sheathes 242 described and shown herein). In some examples, pulling the sheath 642 past the housing 12 and/or the header 14 of the device 10 separates the sheath 642 and causes a split 641 to propagate along the sheath 642, as seen in FIG. 6C. In some examples, the sheath 642 is configured to split, rip, or otherwise separate from a proximal sheath end to a distal sheath end to allow the sheath portion 640 to be removed proximally from the patient around the housing 12 and/or the header 14 of the implantable device 10. In some examples, the sheath 642 is configured to split substantially longitudinally along the sheath 642. In some examples, it is contemplated that the sheath 642 is presplit in a manner similar to that described above with respect to the presplit sheathes 242', 242", 342 described and shown herein.

In some examples, one or both of the handle 614 of the dilator portion 610 and the sheath handle 645 are formed to mimic handles or grasping portions of another medical or surgical instrument. For instance, in some examples, the handle 614 and the sheath handle 645 mimic the handle of a surgical clamp, forceps, scissors, or the like.

In some examples, once the apparatus 600 is in place within the patient, the dilator portion 610 can be removed from the sheath portion 640 (FIG. 6B), leaving the sheath portion 640 within the patient. The antenna 16 of the device 10, in some examples, can then be inserted within the passage 644C and/or the lumen of the sheath 642 and the device 10 can be pushed distally into the sheath 642 and into place within the patient by distally pushing the device 10 (FIG. 6C). In some examples, the device 10 can be held to maintain placement of the device 10 within the patient during removal of the sheath portion 640 from within the patient and around the header 14 and/or the housing 12 of the device 10. In some examples, the sheath portion 640 can be removed from within the patient by grasping the sheath handle 645 and pulling the sheath portion 640 proximally (FIG. 6C). Once the sheath portion 640 is removed from within the patient, in some examples, the device 10 is left in place within the patient.

Figure 7A:
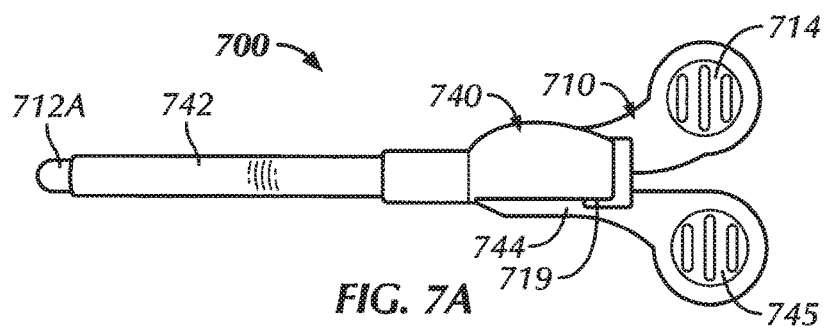
FIGS. 7A-7C show an apparatus for subcutaneously insulting an implantable device within a patient in accordance with at least one example of the invention.
Figure 7B:
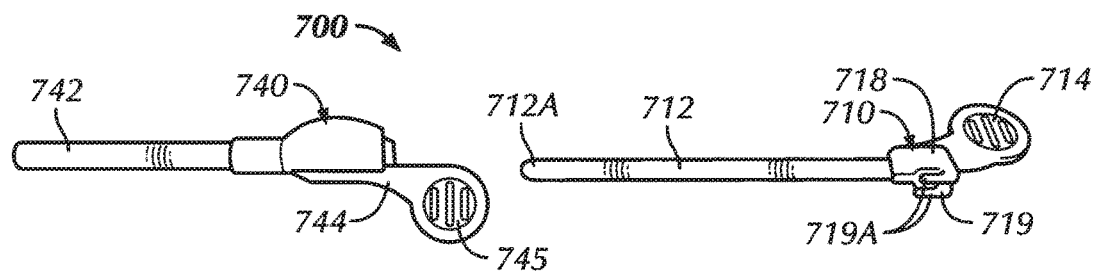
Figure 7C:
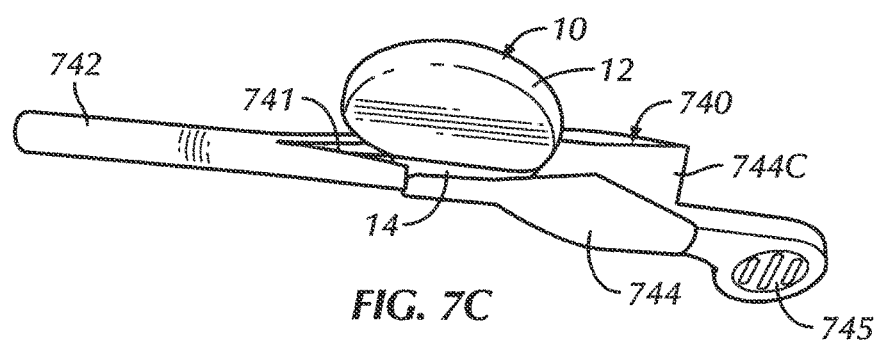

Referring to FIGS. 7A-7C, in some examples, an apparatus 700 is configured for aiding in the subcutaneous implantation within a patient of a device, such as, but not limited to a medical device. In some examples, the apparatus 700 is configured to create a subcutaneous pocket or other space within the patient in order to implant a device, such as the device 10, within the patient. In some examples, the apparatus 700 can be used to assist in implantation of a device, such as the device 10.

In some examples, the apparatus 700 includes a dilator portion 710 and a sheath portion 740. The dilator portion 710 and the sheath portion 740, in some examples, are configured such that the dilator portion 710 and the sheath portion 740 selectively couple together, as shown in FIG. 7A. In some examples, a handle 714 includes a portion 718 complementary to a passage 744C of a sheath housing 744 to fit within the passage 744C with a dilator 712 disposed within a sheath 742. In some examples, the sheath housing 744 and/or the passage of the sheath housing 744 includes a funnel-like configuration to facilitate insertion of the antenna 16 of the device 10 within the passage and the sheath 742. In some examples, the passage of the sheath housing 744 includes a funnel shape configured to facilitate insertion of the antenna 16 within a sheath lumen. In some examples, the sheath portion 740 includes a sheath handle 745 or other gripping portion to facilitate grasping, handling, maneuvering, and the like of the sheath portion 740 during use of the sheath portion 740 by the physician or other caregiver.

In some examples, the dilator portion 710 and the sheath portion 740 are frictionally coupled together, such that the dilator portion 710 and the sheath portion 740 can be selectively uncoupled by a physician or other caregiver using the apparatus 700. In some examples, one of the dilator portion 710 and the sheath portion 740 includes a gripping portion 719 to inhibit unexpected uncoupling of the dilator portion 710 and the sheath portion 740. In some examples, the dilator portion 710 includes a gripping portion 719 sized and shaped to frictionally grip a portion of the sheath portion 740 to inhibit unexpected uncoupling of the dilator portion 710 and the sheath portion 740. In some examples, the gripping portion 719 includes one or more distally-extending fingers 719A to grip the portion of the sheath housing 744. In some examples, the gripping portion 719 is configured to inhibit distal advancement of the dilator portion 710 relative to the sheath portion 740 beyond a desired point. In some examples, the dilator portion 710 is inhibited from being distally advanced with respect to the sheath portion 740 beyond a point at which the handle 714 and the sheath handle 745 substantially line up. In other examples, other connection configurations are contemplated, such as, but not limited to, one or more of a detent configuration, a tab-in-slot configuration, a slidable rail-in-slot configuration, or the like.

In some examples, the dilator 712 terminates at a distal dilator end 712A. In some examples, the distal dilator end 712A includes an atraumatic tip or is otherwise shaped and/or configured to minimize tissue damage or other unwanted effects of using the apparatus 700 to create a subcutaneous pocket in which to implant a device, such as the device 10. In some examples, the dilator 712 is sized to extend distally from the sheath 742 with the dilator portion 710 and the sheath portion 740 coupled together. In some examples, the gripping portion 719 inhibits the dilator portion 710 from being distally advanced with respect to the sheath portion 740 beyond a point at which the distal dilator end 712A extends just beyond a distal end of the sheath 742.

Because, in some examples, the housing 12 and/or the header 14 of the implantable device 10 is larger than the sheath lumen, the sheath 742 is configured to allow removal of the sheath 742 from within the patient and past the housing 12 and/or header 14. In some examples, the sheath 742 is splittable with removing of the sheath portion 740 past the device 10 (similar to the splittable sheathes 242 described and shown herein). In some examples, pulling the sheath 742 past the housing 12 and/or the header 14 of the device 10 separates the sheath 742 and causes a split 741 to propagate along the sheath 742, as seen in FIG. 7C. In some examples, the sheath 742 is configured to split, rip, or otherwise separate from a proximal sheath end to a distal sheath end to allow the sheath portion 740 to be removed proximally from the patient around the housing 12 and/or the header 14 of the implantable device 10. In some examples, the sheath 742 is configured to split substantially longitudinally along the sheath 742. In some examples, it is contemplated that the sheath 742 is presplit in a manner similar to that described above with respect to the presplit sheathes 242', 242", 342 described and shown herein.

In some examples, one or both of the handle 714 of the dilator portion 710 and the sheath handle 745 are formed to mimic handles or grasping portions of another medical or surgical instrument. For instance, in some examples, the handle 714 and the sheath handle 745 mimic the handle of a surgical clamp, forceps, scissors, or the like.

In some examples, once the apparatus 700 is in place within the patient, the dilator portion 710 can be removed from the sheath portion 740 (FIG. 7B), leaving the sheath portion 740 within the patient. The antenna 16 of the device 10, in some examples, can then be inserted within the passage 744C and/or the lumen of the sheath 742 and the device 10 can be pushed distally into the sheath 742 and into place within the patient by distally pushing the device 10 (FIG. 7C). In some examples, the device 10 can be held to maintain placement of the device 10 within the patient during removal of the sheath portion 740 from within the patient and around the header 14 and/or the housing 12 of the device 10. In some examples, the sheath portion 740 can be removed from within the patient by grasping the sheath handle 745 and pulling the sheath portion 740 proximally. Once the sheath portion 740 is removed from within the patient, in some examples, the device 10 is left in place within the patient.

Figure 8A:
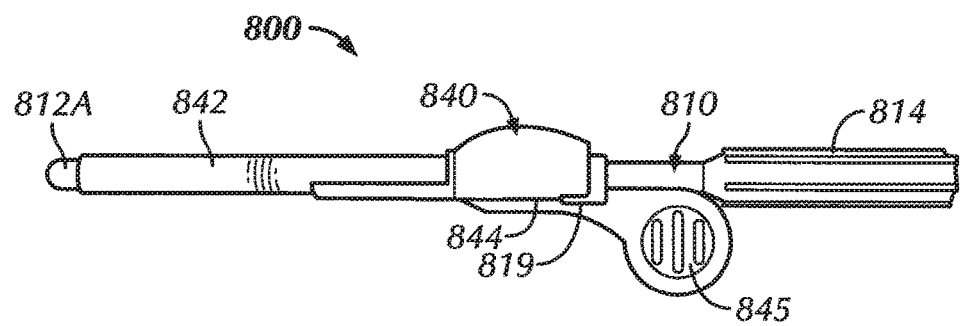
FIGS. 8A-8C show an apparatus for subcutaneously inserting an implantable device within a patient in accordance with at least one example of the invention.
Figure 8B:
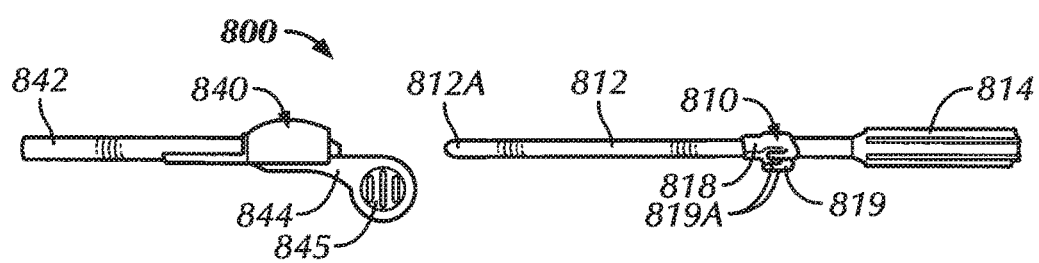
Figure 8C:
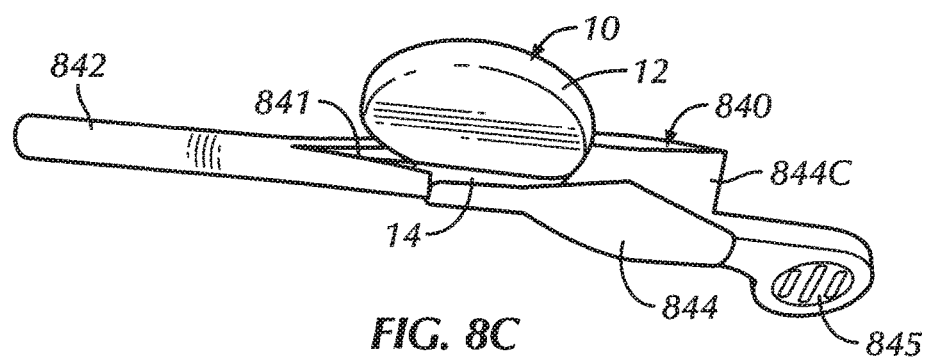

Referring to FIGS. 8A-8C, in some examples, an apparatus 800 is configured for aiding in the subcutaneous implantation within a patient of a device, such as, but not limited to a medical device. In some examples, the apparatus 800 is configured to create a subcutaneous pocket or other space within the patient in order to implant a device, such as the device 10, within the patient. In some examples, the apparatus 800 can be used to assist in implantation of a device, such as the device 10.

In some examples, the apparatus 800 includes a dilator portion 810 and a sheath portion 840. The dilator portion 810 and the sheath portion 840, in some examples, are configured such that the dilator portion 810 and the sheath portion 840 selectively couple together, as shown in FIG. 8A. In some examples, a handle 814 includes a portion 818 complementary to a passage 844C of a sheath housing 844 to fit within the passage 844C with a dilator 812 disposed within a sheath 842. In some examples, the sheath housing 844 and/or the passage of the sheath housing 844 includes a funnel-like configuration to facilitate insertion of the antenna 16 of the device 10 within the passage and the sheath 842. In some examples, the passage of the sheath housing 844 includes a funnel shape configured to facilitate insertion of the antenna 16 within a sheath lumen. In some examples, the sheath portion 840 includes a sheath handle 845 or other gripping portion to facilitate grasping, handling, maneuvering, and the like of the sheath portion 840 during use of the sheath portion 840 by the physician or other caregiver.

In some examples, the dilator portion 810 and the sheath portion 840 are frictionally coupled together, such that the dilator portion 810 and the sheath portion 840 can be selectively uncoupled by a physician or other caregiver using the apparatus 800. In some examples, one of the dilator portion 810 and the sheath portion 840 includes a gripping portion 819 to inhibit unexpected uncoupling of the dilator portion 810 and the sheath portion 840. In some examples, the dilator portion 810 includes a gripping portion 819 sized and shaped to frictionally grip a portion of the sheath portion 840 to inhibit unexpected uncoupling of the dilator portion 810 and the sheath portion 840. In some examples, the gripping portion 819 includes one or more distally-extending fingers 819A to grip the portion of the sheath housing 844. In some examples, the gripping portion 819 is configured to inhibit distal advancement of the dilator portion 810 relative to the sheath portion 840 beyond a desired point. In some examples, the dilator portion 810 is inhibited from being distally advanced with respect to the sheath portion 840 beyond a point at which gripping of the handle 814 becomes blocked, obscured, or otherwise made difficult by the sheath handle 845 or another portion of the sheath portion 540. In other examples, other connection configurations are contemplated, such as, but not limited to, one or more of a detent configuration, a tab-in-slot configuration, a slidable rail-in-slot configuration, or the like.

In some examples, the dilator 812 terminates at a distal dilator end 812A. In some examples, the distal dilator end 812A includes an atraumatic tip or is otherwise shaped and/or configured to minimize tissue damage or other unwanted effects of using the apparatus 800 to create a subcutaneous pocket in which to implant a device, such as the device 10. In some examples, the dilator 812 is sized to extend distally from the sheath 842 with the dilator portion 810 and the sheath portion 840 coupled together. In some examples, the gripping portion 819 inhibits the dilator portion 810 from being distally advanced with respect to the sheath portion 840 beyond a point at which the distal dilator end 812A extends just beyond a distal end of the sheath 842.

Because, in some examples, the housing 12 and/or the header 14 of the implantable device 10 is larger than the sheath lumen, the sheath 842 is configured to allow removal of the sheath 842 from within the patient and past the housing 12 and/or header 14. In some examples, the sheath 842 is splittable with removing of the sheath portion 840 past the device 10 (similar to the splittable sheathes 242 described and shown herein). In some examples, pulling the sheath 842 past the housing 12 and/or the header 14 of the device 10 separates the sheath 842 and causes a split 841 to propagate along the sheath 842, as seen in FIG. 8C. In some examples, the sheath 842 is configured to split, rip, or otherwise separate from a proximal sheath end to a distal sheath end to allow the sheath portion 840 to be removed proximally from the patient around the housing 12 and/or the header 14 of the implantable device 10. In some examples, the sheath 842 is configured to split substantially longitudinally along the sheath 842. In some examples, it is contemplated that the sheath 842 is presplit in a manner similar to that described above with respect to the presplit sheathes 242', 242", 342 described and shown herein.

In some examples, one or both of the handle 814 of the dilator portion 810 and the sheath handle 845 are formed to mimic handles or grasping portions of another medical or surgical instrument. For instance, in some examples, the handle 814 mimics the handle of a tunneling tool or the like. In some examples, the sheath handle 845 mimics the handle of a surgical clamp, forceps, scissors, or the like.

In some examples, once the apparatus 800 is in place within the patient, the dilator portion 810 can be removed from the sheath portion 840 (FIG. 8B), leaving the sheath portion 840 within the patient. The antenna 16 of the device 10, in some examples, can then be inserted within the passage 844C and/or the lumen of the sheath 842 and the device 10 can be pushed distally into the sheath 842 and into place within the patient by distally pushing the device 10 (FIG. 8C). In some examples, the device 10 can be held to maintain placement of the device 10 within the patient during removal of the sheath portion 740 from within the patient and around the header 14 and/or the housing 12 of the device 10. In some examples, the sheath portion 840 can be removed from within the patient by grasping the sheath handle 845 and pulling the sheath portion 840 proximally. Once the sheath portion 840 is removed from within the patient, in some examples, the device 10 is left in place within the patient.

Figure 9A:
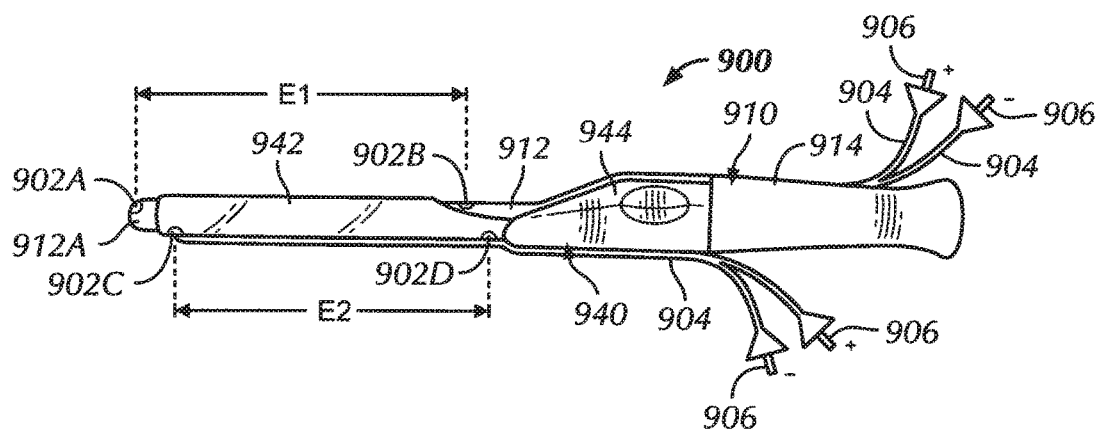
FIGS. 9A and 9B each show an apparatus for subcutaneously inserting an implantable device within a patient in accordance with at least one example of the invention.
Figure 9B:
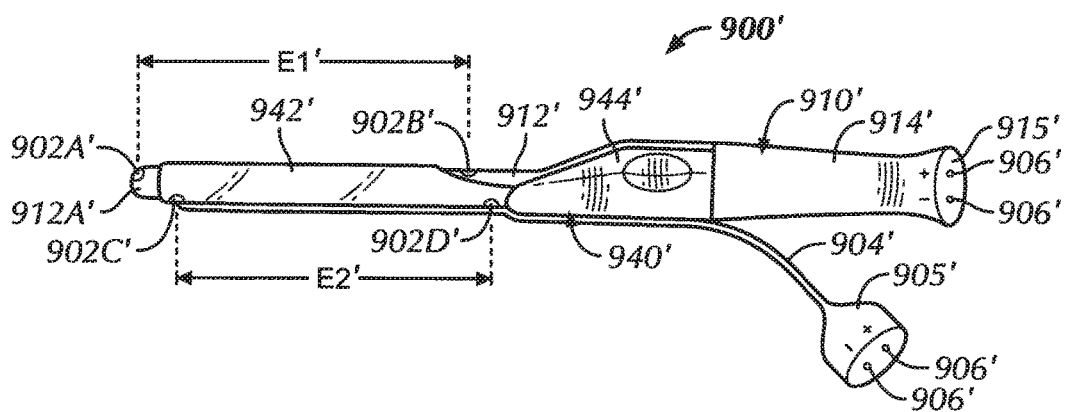

Referring to FIGS. 9A and 9B, in some examples, apparatuses 900, 900' are configured for aiding in the subcutaneous implantation of a device, such as, but not limited to a medical device, within a patient. In some examples, the apparatuses 900, 900' are each configured to create a subcutaneous pocket or other space within the patient in order to implant a device, such as the device 10, within the patient. In some examples, the apparatuses 900, 900' can be used to assist in implantation of a device, such as the device 10. It is noted that the apparatuses 900, 900' are similar to the apparatus 200 described herein. That said, the following description and subject matter related to apparatuses 900, 900' can relate to and be used with any of the apparatuses 200, 300, 400, 500, 600, 700, 800 described herein.

Similar to apparatus 200, in some examples, the apparatus 900, 900' includes a removable dilator portion 910, 910' removably engageable with a sheath portion 940, 940'. In some examples, the dilator portion 910, 910' includes a dilator 912, 912' including a distal dilator end 912A, 912A'. In some examples, the dilator portion 910, 910' includes a handle 914, 914' disposed at a proximal end of the dilator portion 910, 910'. In some examples, the sheath portion 940, 940' includes a sheath housing 944, 944' attached to a proximal end of a sheath 942, 942'. In various examples, the sheath 942, 942' can be configured to be splittable or presplit, as described herein. In some examples, the apparatus 900, 900' includes electrodes 902, 902' to sense physiologic signal from and/or stimulate the tissue of the patient, and replicate, or otherwise approximate, electrode spacing and placement of the device 10 (FIG. 1). Although shown in FIGS. 9A and 9B with four electrodes 902, 902', it is contemplated that, in other examples, the apparatus 900, 900' includes more or less than four electrodes 902, 902'.

For instance, in some examples, the apparatus 900, 900' can include two electrodes to sense a physiologic signal from and/or stimulate the tissue of the patient, and replicate, or otherwise approximate, electrode spacing and placement of the device 10. In some examples, the apparatus 900, 900' includes two electrodes 902A, 902A', 902B, 902B' disposed on the dilator portion 910, 910' and spaced apart a distance E1, E1', for instance, to simulate, replicate, or otherwise approximate electrode spacing and placement of the device 10. In other examples, the apparatus 900, 900' includes two electrodes 902C, 902C', 902D, 902D' disposed on the sheath portion 940, 940' and spaced apart a distance E2, E2', for instance, to simulate, replicate, or otherwise approximate electrode spacing and placement of the device 10. In still other examples, the apparatus 900, 900' includes the two electrodes 902A, 902A', 902B, 902B' disposed on the dilator portion 910, 910' and the two electrodes 902C, 902C', 902D, 902D' disposed on the sheath portion 940, 940'. In other examples, the apparatus 900, 900' includes more than four electrodes disposed at various locations on the dilator portion 910, 910' and/or the sheath portion 940, 940'.

In some examples, the apparatus 900, 900' includes conductors 904, 904' from the electrodes 902A, 902A', 902B, 902B', 902C, 902C', 902D, 902D' to connectors 906, 906'. In some examples, the connectors 906, 906' are configured to be electrically coupled to an external test device or signal generator. In some examples, referring briefly to FIG. 9A, the connectors 906 are male connectors 906 configured to be plugged into female connectors of the test device or signal generator or clasped onto with alligator clips or other clips or attachment devices of the test device or signal generator. In some examples, referring briefly to FIG. 9B, the connectors 906' are female connectors 906' configured to accept male connectors of the test device or signal generator. In some examples, the female connectors 906' are disposed within a hub 905' at the end of the conductor 904'. In some examples, the female connectors 906' are disposed within a hub 915' disposed within the dilator portion 910' (such as within a proximal end of the handle 914, for instance). In some examples, the apparatus 900, 900' can include a combination of male connectors and female connectors. In some examples, the apparatus 900' can include connectors disposed within a second hub extending from the dilator portion 910' (rather than disposed within a hub 915' disposed within the handle 914') in a manner similar to the hub 905'.

In various examples, the electrodes 902A, 902A', 902B, 902B' of the dilator portion 910, 910' and/or the electrodes 902C, 902C', 902D, 902D' of the sheath portion 940, 940' are located and spaced to replicate electrode spacing and placement of the device 10 to allow the physician or other caregiver the opportunity to test the implant location for the electrodes of the device 10 prior to actually implanting the device 10. That is, in some examples, with the apparatus 900, 900' located at least partially within the patient at the desired implant site, the apparatus 900, 900' can be electrically coupled to a test device or other device (for instance, by coupling connectors of the test device to the connectors 906, 906' of the apparatus 900, 900') to verify or otherwise test or verify a signal at that location within the patient prior to actually implanting the device 10. In this way, the signal can be verified, and, if the test signal is deemed unsatisfactory, the physician or other caregiver can relocate the apparatus 900, 900' and test again until the signal is deemed satisfactory, at which point the device 10 can be implanted. This can lessen, if not eliminate, the possibility of implanting the device 10 in a location and/or position within the patient that produces a weak or otherwise unsatisfactory signal.

The present inventors have recognized various advantages of the subject matter described herein. For instance, in some examples, the apparatuses, systems, and methods described herein can be used to subcutaneously implant a device. The present inventors have further recognized, among other things, that the present subject matter, in various examples, can provide a simpler approach to insertion, shorter insertion time, reduced risk of complications, reduced expense, and/or a reduced need for expensive equipment, such as fluoroscopy, during device placement. While various advantages of the example apparatuses, systems, and methods are listed herein, this list is not considered to be complete, as further advantages may become apparent from the description and figures presented herein.

Although the subject matter of the present patent application has been described with reference to various examples, workers skilled in the art will recognize that changes can be made in form and detail without departing from the scope of the subject matter recited in the below claims.

The above Detailed Description includes references to the accompanying drawings, which form a part of the Detailed Description. The drawings show, by way of illustration, specific examples in which the present apparatuses and methods can be practiced. These embodiments are also referred to herein as "examples."

The above Detailed Description is intended to be illustrative, and not restrictive. For example, the above-described examples (or one or more elements thereof) can be used in combination with each other. Other embodiments can be used, such as by one of ordinary skill in the art upon reviewing the above description. Also, various features or elements can be grouped together to streamline the disclosure. This should not be interpreted as intending that an unclaimed disclosed feature is essential to any claim. Rather, inventive subject matter can lie in less than all features of a particular disclosed embodiment. Thus, the following claims are hereby incorporated into the Detailed Description, with each claim standing on its own as a separate embodiment. The scope of the invention should be determined with reference to the appended claims, along with the full scope of equivalents to which such claims are entitled.

In this document, the terms "a" or "an" are used to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "about" and "approximately" or similar are used to refer to an amount that is nearly, almost, or in the vicinity of being equal to a stated amount.

In the appended claims, the terms "including" and "in which" are used as the plain-English equivalents of the respective terms "comprising" and "wherein." Also, in the following claims, the terms "including" and "comprising" are open-ended, that is, an apparatus or method that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to allow the reader to quickly ascertain the nature of the technical disclosure. It is submitted with the understanding that it will not be used to interpret or limit the scope or meaning of the claims.

The invention claimed is:

1. An apparatus for subcutaneously inserting an implantable device within a patient, the implantable device including a housing and an antenna extending outwardly from the housing, the antenna including an antenna length, the apparatus comprising:
   a dilator portion including a dilator including a dilator length, the dilator portion being configured to separate tissue to create a subcutaneous pocket within the patient sized and shaped to accommodate the implantable device within the subcutaneous pocket; and
   a sheath portion including:
      a sheath sized and shaped to accommodate the dilator within a sheath lumen, the sheath configured to accommodate the antenna of the implantable device with the dilator removed from within the sheath; and
      a sheath housing at a proximal sheath end, the sheath housing including a passage substantially aligned with the sheath lumen, wherein the sheath includes a sheath length that is at least substantially as long as the antenna length, the sheath including a substantially longitudinal split extending from the proximal sheath end to a distal sheath end, the substantially longitudinal split being formed between a first edge and a second edge, the first edge overlapping but not interlocking with the second edge to form a substantially tubular shape for the sheath, wherein the sheath is configured to spread apart along the substantially longitudinal split to allow removal of the sheath past the housing of the implantable device to remove the sheath from and leave the implantable device within the subcutaneous pocket within the patient, the sheath housing including an opening along a side of the sheath housing to allow access to the passage from the side of the sheath housing, the opening and the passage being configured to allow the housing of the implantable device to pass through the sheath housing without splitting the sheath housing, and wherein the sheath portion includes an intermediate sheath opening disposed between a proximal end of the sheath housing and the substantially longitudinal split of the sheath, wherein, with the dilator portion removed from the sheath portion, the passage permits movement of the implantable device into the sheath portion to a position residing in the intermediate sheath opening with the antenna residing in the sheath lumen.

2. The apparatus of claim 1, wherein the dilator portion includes a handle configured to separate tissue to create the subcutaneous pocket, such that:
   the dilator portion is configured to create a portion of the subcutaneous pocket configured to accommodate the antenna of the device; and
   the handle is configured to create a portion of the subcutaneous pocket configured to accommodate the housing of the device.

3. The apparatus of claim 1, wherein the passage of the sheath housing is fluidly coupled with the sheath lumen.

4. The apparatus of claim 1, wherein the dilator portion includes a handle, the handle having a portion complementary to the passage of the sheath housing to fit within the passage with the dilator disposed within the sheath.

5. The apparatus of claim 1, wherein the passage of the sheath housing includes a funnel shape configured to facilitate insertion of the antenna within the sheath lumen.

6. The apparatus of claim 1, wherein the sheath housing includes a first material and the sheath includes a second material, the first material being different than the second material.

7. The apparatus of claim 1, wherein the dilator includes a distal dilator end including an atraumatic shape, the dilator length being longer than the sheath length to allow the distal dilator end to extend distally from the sheath.

8. The apparatus of claim 1, comprising at least two electrodes configured to electrically couple to a test device, the electrodes being configured to verify a signal at a location within the patient prior to implantation of the implantable device.

9. The apparatus of claim 8, wherein the at least two electrodes are disposed on the sheath portion.

10. The apparatus of claim 1, wherein the sheath is formed from fluorinated ethylene propylene (FEP).

11. The apparatus of claim 1, wherein the opening is substantially aligned with the substantially longitudinal split to allow the housing of the implantable device to pass through the opening and the substantially longitudinal split with removal of the sheath portion from the implantable device.

12. The apparatus of claim 1, wherein the passage and the opening of the sheath housing form a channel-like configuration of the sheath housing.

13. The apparatus of claim 1, wherein the sheath housing is substantially U-shaped when viewed from a proximal end of the sheath housing.

14. An apparatus for subcutaneously inserting an implantable device within a patient, the implantable device including a housing and an antenna extending outwardly from the housing, the antenna including an antenna length, the apparatus comprising:
   a dilator portion including a dilator including a dilator length, the dilator portion being configured to separate tissue to create a subcutaneous pocket within the patient sized and shaped to accommodate the implantable device within the subcutaneous pocket; and
   a sheath portion including:
      a sheath sized and shaped to accommodate the dilator within a sheath lumen, the sheath configured to accommodate the antenna of the implantable device with the dilator removed from within the sheath, wherein the sheath includes a sheath length that is at least substantially as long as the antenna length, the sheath including a substantially longitudinal split extending from a proximal sheath end to a distal sheath end, the substantially longitudinal split being formed between a first edge and a second edge, the first edge overlapping but not interlocking with the second edge to form a substantially tubular shape for the sheath; and a sheath housing disposed at the proximal sheath end, the sheath housing including a passage fluidly coupled with the sheath lumen at a sheath housing distal end and extending through the sheath housing to a sheath housing proximal end, the sheath housing including an opening in a sidewall of the sheath housing to allow access to the passage from the side of the sheath housing, the opening and the passage being configured to allow the housing of the implantable device to pass through the sheath housing without splitting the sheath housing, wherein the sheath is configured to spread apart along the substantially longitudinal split along a separation line substantially aligning with the opening in the sidewall of the sheath housing, the separation line and the opening cooperating to allow the housing to pass through the opening and the separated sheath with removal of the sheath from the implantable device to leave the implantable device within the subcutaneous pocket within the patient, and wherein the sheath portion includes an intermediate sheath opening disposed between the sheath housing proximal end and the substantially longitudinal split of the sheath, wherein, with the dilator portion removed from the sheath portion, the passage permits movement of the implantable device into the sheath portion to a position residing in the intermediate sheath opening with the antenna residing in the sheath lumen.

15. The apparatus of claim 14, wherein the dilator portion includes a handle configured to separate tissue to create the subcutaneous pocket, such that:

the dilator portion is configured to create a portion of the subcutaneous pocket configured to accommodate the antenna of the device; and the handle is configured to create a portion of the subcutaneous pocket configured to accommodate the housing of the device.

16. The apparatus of claim 14, comprising at least two electrodes disposed on the sheath portion configured to electrically couple to a test device, the electrodes being configured to verify a signal at a location within the patient prior to implantation of the implantable device.

17. The apparatus of claim 14, wherein the sheath is formed from fluorinated ethylene propylene (FEP).

18. The apparatus of claim 14, wherein the passage and the opening of the sheath housing form a channel-like configuration of the sheath housing, such that the sheath housing is substantially U-shaped when viewed from a proximal end of the sheath housing.

* * * * *